(12) United States Patent
Frankle et al.

(10) Patent No.: US 10,835,383 B2
(45) Date of Patent: *Nov. 17, 2020

(54) GLENOSPHERE WITH FLANGE FOR AUGMENTED FIXATION AND RELATED METHODS

(71) Applicant: Encore Medical, L.P., Austin, TX (US)

(72) Inventors: Mark A. Frankle, Tampa, FL (US); Sergio Gutierrez, Tampa, FL (US); Gerald Williams, Tampa, FL (US)

(73) Assignee: Encore Medical, L.P., Austin, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/314,025

(22) PCT Filed: Jul. 12, 2017

(86) PCT No.: PCT/US2017/041753
§ 371 (c)(1),
(2) Date: Dec. 28, 2018

(87) PCT Pub. No.: WO2018/013712
PCT Pub. Date: Jan. 18, 2018

(65) Prior Publication Data
US 2019/0192305 A1      Jun. 27, 2019

Related U.S. Application Data

(63) Continuation-in-part of application No. 15/376,334, filed on Dec. 12, 2016, now Pat. No. 9,782,263, and
(Continued)

(51) Int. Cl.
*A61F 2/40*      (2006.01)
*A61F 2/30*      (2006.01)
*A61B 17/86*     (2006.01)

(52) U.S. Cl.
CPC ........ *A61F 2/4081* (2013.01); *A61F 2/30749* (2013.01); *A61F 2/40* (2013.01);
(Continued)

(58) Field of Classification Search
CPC .. A61F 2/40; A61F 2/4081; A61F 2002/4085; A61F 2002/4062
See application file for complete search history.

(56) References Cited

U.S. PATENT DOCUMENTS

| 6,416,553 B1 | 7/2002 | White |
| 6,790,234 B1 | 9/2004 | Frankle |

(Continued)

FOREIGN PATENT DOCUMENTS

| DE | 102005001256 | 2/2006 |
| EP | 1064890 | 9/2005 |

OTHER PUBLICATIONS

International Search Report in International Patent Application No. PCT/US2017/041753, dated Nov. 17, 2017 (4 pages).
(Continued)

*Primary Examiner* — Jason-Dennis N Stewart
(74) *Attorney, Agent, or Firm* — Nixon Peabody LLP

(57) ABSTRACT

A glenosphere includes a body and a flange. The body includes a first body surface and a spherical second body surface, and includes an engagement feature to engage with an attachment structure attachable to a bone. The flange extends radially outward from the body and includes a first flange surface contiguous with a first body surface and a second flange surface contiguous with the second body surface. The flange has a flange length extending from a first end and a second end such that an angle defined by a first line from a center of the body to the first end and a second line from the center of the body to the second end is less than 180 degrees.

20 Claims, 28 Drawing Sheets

Related U.S. Application Data a continuation-in-part of application No. 15/257,226, filed on Sep. 6, 2016, now Pat. No. 10,226,350, and a continuation-in-part of application No. 15/211,518, filed on Jul. 15, 2016, now Pat. No. 9,795,490.

(52) U.S. Cl.
CPC ....... *A61B 17/86* (2013.01); *A61F 2002/3065* (2013.01); *A61F 2002/3085* (2013.01); *A61F 2002/30245* (2013.01); *A61F 2002/30331* (2013.01); *A61F 2002/30332* (2013.01); *A61F 2002/30433* (2013.01); *A61F 2002/30578* (2013.01); *A61F 2002/30777* (2013.01); *A61F 2002/30785* (2013.01); *A61F 2002/30787* (2013.01); *A61F 2002/4085* (2013.01)

(56) References Cited

U.S. PATENT DOCUMENTS

| | | |
|---|---|---|
| 7,918,896 B2 | 4/2011 | DeSmet |
| 2007/0244563 A1 | 10/2007 | Roche |
| 2009/0149961 A1 | 6/2009 | Dallmann |
| 2010/0057128 A1 | 3/2010 | Bullard |
| 2010/0125336 A1 | 5/2010 | Johnson |
| 2012/0029647 A1 | 2/2012 | Winslow |
| 2013/0204375 A1 | 8/2013 | Winslow |
| 2013/0261751 A1 | 10/2013 | Lappin |
| 2015/0142122 A1 | 5/2015 | Bickley |
| 2016/0166297 A1 | 6/2016 | Mighell |

OTHER PUBLICATIONS

Written Opinion in International Patent Application No. PCT/US2017/041753, dated Nov. 17, 2017 (10 pages).

GLENOSPHERE WITH FLANGE FOR AUGMENTED FIXATION AND RELATED METHODS

CROSS-REFERENCE TO RELATED APPLICATIONS

This application is a U.S. National Stage of International Application No. PCT/US2017/041753, filed Jul. 12, 2017, which is a continuation-in-part of U.S. patent application Ser. No. 15/211,518, filed Jul. 15, 2016, now U.S. Pat. No. 9,795,490; International Application No. PCT/US2017/041753 is also a continuation-in-part of U.S. patent application Ser. No. 15/257,226, filed Sep. 6, 2016, now allowed; International Application No. PCT/US2017/041753 is also a continuation-in-part of U.S. patent application Ser. No. 15/376,334, filed Dec. 12, 2016, now U.S. Pat. No. 9,782,263, each of which is hereby incorporated by reference herein in its entirety.

TECHNICAL FIELD

The present disclosure generally relates to the field of shoulder replacement surgery, and more specifically to apparatuses, systems, and methods relating to shoulder replacement using a glenosphere.

BACKGROUND

Shoulder replacement surgeries (e.g., total shoulder arthroplasty (TSA) and reverse shoulder arthroplasty (RSA)) are performed to repair a patient's shoulder joint, such as when joints have been damaged or lose functionality due to disease, bone loss, or other trauma. In some surgeries, a glenosphere acts as a connecting element between the patient's humerus and scapula, and may be oriented at an anatomic orientation to mimic the ball-and-joint configuration and movement of a natural shoulder joint. A base plate may be positioned between the glenosphere and the scapula, and a bone graft may be used to facilitate joining the base plate and glenosphere to the scapula. However, even with a bone graft, glenoid bone loss or other deterioration of the shoulder joint even after a shoulder replacement surgery may cause additional problems, reducing the effectiveness of the shoulder replacement surgery.

SUMMARY

According to an aspect of the present disclosure, a glenosphere includes a body and a flange. The body includes a first body surface and a spherical second body surface, and includes an engagement feature to engage with an attachment structure attachable to a bone. The flange extends radially outward from the body and includes a first flange surface contiguous with a first body surface and a second flange surface contiguous with the second body surface. The flange has a flange length extending from a first end and a second end such that an angle defined by a first line from a center of the body to the first end and a second line from the center of the body to the second end is less than 180 degrees.

According to another aspect of the present disclosure, a shoulder prosthesis system includes a plate and a glenosphere. The plate is configured to be attached to a portion of a shoulder bone. The plate includes a plate body including a first plate surface and a second plate surface opposite the first plate surface. The plate includes an engagement member extending from the second plate surface. The plate is configured to receive a plurality of plate fixation members. The plurality of plate fixation members are configured to attach the plate to the portion of the shoulder bone. The glenosphere includes a body and a flange. The body includes a first body surface and a spherical second body surface, and includes an engagement feature to engage with an attachment structure attachable to a bone. The flange extends radially outward from the body and includes a first flange surface contiguous with a first body surface and a second flange surface contiguous with the second body surface. The flange has a flange length extending from a first end and a second end such that an angle defined by a first line from a center of the body to the first end and a second line from the center of the body to the second end is less than 180 degrees.

According to another aspect of the present disclosure, a glenosphere includes a body and a flange. The body includes a first body surface and a spherical second body surface and includes an engagement feature to engage with an attachment structure attachable to a bone. The flange is integral with the body, extends radially outward from the body and includes a first flange surface contiguous with the first body surface and a second flange surface contiguous with the second body surface. The flange has a flange length extending from a first end and a second end such that an angle defined by a first line from a center of the body to the first end and a second line from the center of the body to the second end is less than 180 degrees.

According to another aspect of the present disclosure, a glenosphere for use in a shoulder prosthesis includes a body, a first surface, and a cavity defined with the body. The body defines a center and an engagement axis passing through the body, the engagement axis spaced by an offset from the center. The first surface includes a first rim and a second rim. The first rim is positioned radially outward from the second rim. The first surface includes a base surface portion and a hood surface portion extending from the base surface portion and oriented at an obtuse angle relative to the base surface portion. The body defines a hood portion extending from the hood surface portion to a plane including the base surface portion. The cavity has a perimeter defined by the second rim. The cavity includes a first cavity portion configured to receive an attachment structure attachable to a bone, and a second cavity portion configured to engage an engagement member of the attachment structure. The second cavity portion is oriented along the engagement axis.

According to another aspect of the present disclosure, a shoulder prosthesis system includes a plate and a glenosphere. The plate is configured to be attached to a portion of a shoulder bone. The plate includes a plate body including a first plate surface and a second plate surface opposite the first plate surface. The plate includes an engagement member extending from the second plate surface. The plate is configured to receive a plurality of plate fixation members. The plurality of plate fixation members are configured to attach the plate to the portion of the shoulder bone. The glenosphere includes a glenosphere body, a first glenosphere surface, and a cavity. The glenosphere body defines a center and an engagement axis passing through the glenosphere body. The engagement axis is spaced by an offset from the center. The first glenosphere surface includes a first rim and a second rim. The first rim is positioned radially outward from the second rim. The first glenosphere surface includes a glenosphere base surface portion and a glenosphere hood surface portion extending from the glenosphere base surface portion and oriented at an obtuse angle relative to the glenosphere base surface portion. The cavity is defined within the glenosphere body. The cavity has a perimeter defined by the second rim. The cavity includes a first cavity portion configured to receive the plate and a second cavity portion configured to engage the engagement member of the plate. The second cavity portion is oriented along the engagement axis.

According to another aspect of the present disclosure, a glenosphere for use in a shoulder prosthesis includes a body, a first surface, a second articulating surface, and a plurality of channels. The body includes a baseplate engagement region, and defines a center of rotation. The baseplate engagement region includes an engager defining an engagement axis offset from the center of rotation. The first surface is outward from the baseplate engagement region and includes a first rim. The second articulating surface extends from the first rim of the first surface. The second surface has a convex shape. The plurality of channels extend from the first surface through the body to the second surface. Each channel of the plurality of channels defines a first opening positioned on a same side of the first surface relative to a plane including the engagement axis. Each channel defines a channel axis extending through the corresponding channel. Each channel axis is radially outward from the engagement axis and spaced from the baseplate engagement region. Each channel is configured to receive a bone fixation member configured to secure the glenosphere to the bone.

According to another aspect of the present disclosure, a glenosphere includes a spherical body. The spherical body includes a first edge that defines a complete path about the body, a first surface extending from a first side of the first edge, and a second surface extending from a second side of the first edge opposite the first side. The spherical body defines a center such that each point on the first surface is equidistant from the center. The first edge defines a first point and a second point. A first shortest path between the first point and the second point along the first surface is greater than half of a circumference of a spherical region defined by all points equidistant from the center.

According to another aspect of the present disclosure, a glenosphere for use in a shoulder prosthesis includes a body, a first surface, a second surface, a cavity defined within the body, and a plurality of channels. The body defines a central axis passing through the body. The first surface includes a first rim and a second rim. The first rim is positioned radially outward from the second rim relative to the central axis. The second surface extends from the first rim of the first surface. The second surface has a convex shape. The cavity has a perimeter defined by the second rim and is configured to receive an attachment structure attachable to a bone. The plurality of channels extend from the first surface through the body to the second surface. Each channel defines a first opening positioned on the first surface between the first rim and the second rim and defines a second opening positioned on the second surface. Each channel is configured to receive a bone fixation member configured to secure the glenosphere to the bone.

According to another aspect of the present disclosure, a shoulder prosthesis system includes a plate, a glenosphere, and a plurality of glenosphere fixation members. The plate is configured to be fixated to a portion of a shoulder bone. The plate includes a plate body including a first plate surface and a second plate surface opposite the first plate surface. The plate is configured to receive a plurality of plate fixation members. The plurality of plate fixation members are configured to attach the plate to the portion of the shoulder bone. The glenosphere includes a glenosphere body defining a central axis passing through the glenosphere body. The glenosphere includes a first glenosphere body surface including a first rim and a second rim. The first rim is positioned radially outward from the second rim relative to the central axis. The glenosphere includes a second glenosphere body surface extending from the first rim of the first body surface. The second glenosphere body surface has a convex shape. The glenosphere includes a cavity defined within the body. The cavity has a perimeter defined by the second rim. The cavity is configured to receive the plate. The glenosphere includes a plurality of channels extending from the first glenosphere body surface through the glenosphere body to the second glenosphere body surface. Each channel defines a first opening positioned on the first glenosphere body surface between the first rim and the second rim. Each channel defines a second opening positioned on the second glenosphere body surface. Each channel is configured to receive a glenosphere fixation member. The glenosphere fixation members are configured to secure the glenosphere to the portion of the shoulder bone to augment fixation of the shoulder prosthesis system to the shoulder bone.

According to another aspect of the present disclosure, a method of securing a glenosphere to a portion of a shoulder bone and to a plate fixated to the portion of the shoulder bone includes positioning the glenosphere adjacent to the plate. The glenosphere includes a body defining a central axis passing through the body, a first surface including a first rim and a second rim, a second surface extending from the first rim of the first surface, the second surface having a convex shape, a cavity extending into the body from the first surface, the cavity configured to receive the plate, and a plurality of channels extending from the first surface through the body to the second surface. Each channel defines a first opening positioned on the first surface between the first rim and the second rim, defines a second opening positioned on the second surface, and defines a channel axis passing through the channel. The method includes orienting the glenosphere relative to the plate such that each channel axis is positioned to be outside an interference space defined by one or more plate fixation members received by the plate into the portion of the shoulder bone. The method includes receiving the plate into the cavity. The method includes receiving a plurality of glenosphere fixation members in the plurality of channels via the plurality of second openings such that the plurality of glenosphere fixation members are positioned outside of the interference space and contact the portion of the shoulder bone. The method includes securing the plurality of glenosphere fixation members to the portion of the shoulder bone.

Some or all of the systems, components, and subcomponents of the present disclosure can be single-use or disposable. Also some or all of the systems, components, and subcomponents of the present disclosure can be made of a unitary construction (formed from a single piece of metal, plastic, or other material) or unitary modular construction (plurality of components and/or subcomponents permanently connected by standard means, such as welding or soldering), or of modular construction (plurality of components and/or subcomponents removably connected by standard means, such as threading or snap-fitting).

These and other features of various embodiments can be understood from a review of the following detailed description in conjunction with the accompanying drawings.

It is to be understood that both the foregoing general description and the following detailed description are explanatory and are not restrictive of the present disclosure, as claimed.

DETAILED DESCRIPTION

Figure 1:
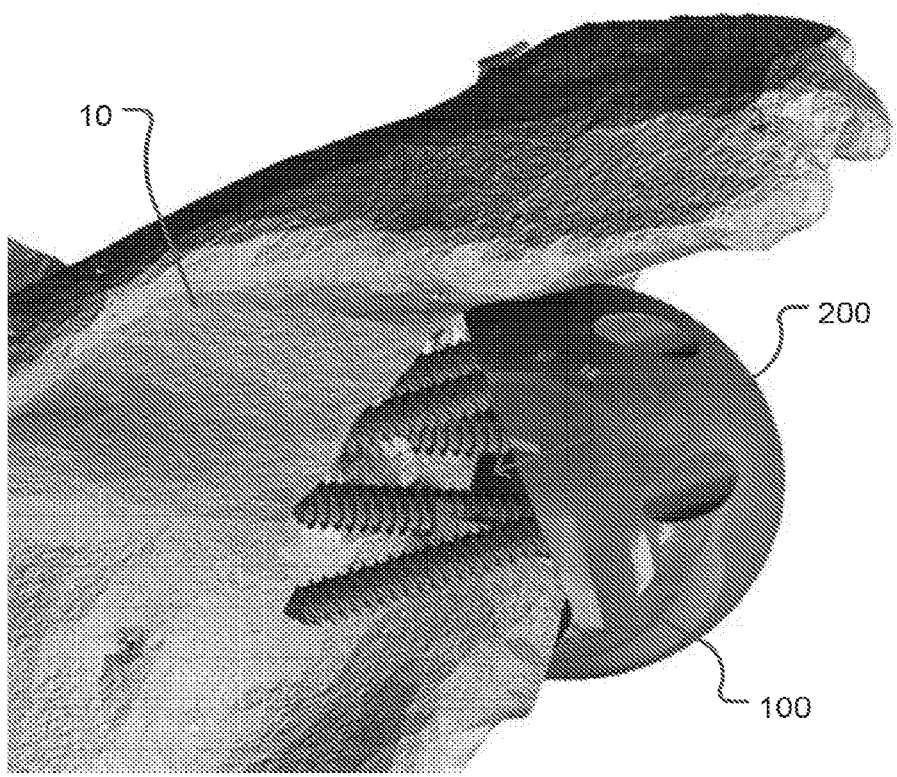
FIG. 1 is a perspective view of an embodiment of a shoulder prosthesis system including a plate and a glenosphere fixated to a portion of a shoulder bone.

The following detailed description and the appended drawings describe and illustrate various glenosphere systems, methods, and components. The description and drawings are provided to enable one of skill in the art to make and use one or more glenosphere systems and/or components, and/or practice one or more methods. They are not intended to limit the scope of the claims in any manner.

The use of "e.g." "etc.," "for instance," "in example," and "or" and grammatically related terms indicates non-exclusive alternatives without limitation, unless otherwise noted. The use of "optionally" and grammatically related terms means that the subsequently described element, event, feature, or circumstance may or may not be present/occur, and that the description includes instances where said element, event, feature, or circumstance occurs and instances where it does not. The use of "attached" and "coupled" and grammatically related terms refers to the fixed, releasable, or integrated association of two or more elements and/or devices with or without one or more other elements in between. Thus, the term "attached" or "coupled" and grammatically related terms include releasably attaching or fixedly attaching two or more elements and/or devices in the presence or absence of one or more other elements in between. As used herein, the terms "proximal" and "distal" are used to describe opposing axial ends of the particular elements or features being described in relation to anatomical placement.

A. Glenosphere with Augmented Fixation and Related Methods

In existing solutions, shoulder replacement devices may lose effectiveness over time due to glenoid bone loss or other deterioration, which may be exacerbated by forces applied to a portion of a shoulder bone by a shoulder prosthesis. Although bone grafts may be used to supplement engagement between a plate contacting the portion of the shoulder bone and the portion of the shoulder bone, the usefulness of the bone grafts may be reduced by bone loss. The present solution provides systems, methods, and apparatuses for improving shoulder prostheses by augmenting fixation of a glenosphere to the portion of the shoulder bone. The glenosphere includes a body, a first surface, a second surface, a cavity, and a plurality of channels. The body defines a central axis passing through the body. The first surface includes a first rim and a second rim. The first rim is positioned radially outward from the second rim relative to the central axis. The second surface extends from the first rim of the first surface. The second surface has a convex shape. The cavity extends into the body from the first surface. The cavity includes a cavity wall extending from the second rim in a direction substantially parallel to the central axis into the body and a cavity surface. The cavity is configured to receive a plate defining an interference space. The plurality of channels extend from the first surface through the body to the second surface. Each channel defines a first opening positioned on the first surface between the first rim and the second rim and defines a second opening positioned on the second surface. Each channel is configured to be oriented to define a channel axis that passes through the channel and is positioned to be outside of the interference space when the plate is received in the cavity. A plurality of glenosphere fixation members can be received through the plurality of channels to secure the glenosphere to the portion of the shoulder bone. As such, fixation of the glenosphere to the shoulder can be augmented, in order to mitigate glenoid bone loss or other changes to the shoulder joint that would otherwise deteriorate the shoulder joint and reduce the effectiveness of the shoulder prosthesis.

Referring to FIG. 1, a perspective view of a shoulder prosthesis including a glenosphere 100 and a plate 200 fixated to a portion 10 of a shoulder bone is shown. The glenosphere 100 is coupled to the plate 200, such as by engagement of an engagement member of the glenosphere 100 and an engagement member of the plate 200. The glenosphere 100 can be oriented and further secured (e.g., fixated, attached, etc.) to the portion 10 outside of portions of bone different from portions of bone at which the plate 200 is attached. In some embodiments, securing the glenosphere to the portion 10 of the shoulder bone reduces stress on the portion 10 of the shoulder bone to mitigate glenoid bone loss damage.

In various embodiments, the glenosphere 100 is configured to be coupled to any of a variety of plates. For example, the plates can include various shapes (e.g., cylindrical, ovoid, rectangular, convex, concave, etc.). The plate can be formed as a single plate (e.g., similar or identical to plate 200 as shown in FIG. 1), or can be formed as a plurality of plates (e.g., a plurality of plates fixed to discrete portions of a shoulder bone). The glenosphere 100 can be configured to couple to plates in various ways, such as by using a variety of fastening members and/or engagement members (e.g., screws, bolts, press fits, frictional engagements, tabs, locks, etc.). In some embodiments, the glenosphere 100 can be configured to include one or more engagement features that are sized, configured or designed to engage with corresponding engagement features of a corresponding plate with which the glenosphere is to be coupled.

In some embodiments, the glenosphere 100 acts as a ball in a ball-and-socket joint between a humerus (not shown) and the shoulder bone. By augmenting the fixation of the glenosphere to the shoulder bone, the present solution can improve the effectiveness of a shoulder prosthesis for a patient, including improving the patient's ability to use their humerus. For example, augmenting the fixation of the glenosphere 100 to the shoulder bone can facilitate orienting the glenosphere 100 in an anatomic orientation, allowing a patient to use their humerus in an anatomic or natural range of motion.

In some embodiments, the glenosphere 100 and plate 200 are provided in a surgical kit or otherwise paired together, such as for being secured to the portion 10 of the shoulder bone in a single procedure. In some embodiments, the plate 200 has already been secured to the portion 10, and the glenosphere 100 is designed to complement the plate 200, to augment fixation of the plate 200, to replace an existing shoulder prosthesis component (e.g., an existing glenosphere), etc. The glenosphere 100 can be customized or otherwise designed to match a particular plate 200. The glenosphere 100 can have broad or universal compatibility with various plates 200.

In some embodiments, the glenosphere 100 is customized or otherwise designed for compatibility with a particular patient. For example, a model of the glenosphere 100 can be generated based on information regarding the shoulder of a patient, such as imaging data (e.g., MRI data, etc.) and/or based on information regarding the plate 200. The information can indicate target locations on the portion 10 for securing the glenosphere 100 to the portion 10. For example, the information can include target locations on a surface of the portion 10 through which fixation members will be driven to secure the glenosphere 100 to the portion 10. The information can indicate an interference space of the plate 200. The information can indicate locations on the portion 10 where bone loss has occurred or may occur, such as for avoiding these locations when securing the glenosphere 100 to the portion 10. For example, based on information regarding the shoulder of the patient and/or the plate 200, the glenosphere 100 can be manufactured such that fixation members used to secure the glenosphere 100 to the portion 10 are positioned outside of the interference space of the plate 200 and enter the portion 10 at locations that are stable with regards to bone loss. In some embodiments, this can be achieved by orienting a plurality of channels of the glenosphere 100 in which the fixation members are received. When the plate 200 is received in the glenosphere 100 and the fixation members are received in the plurality of channels, the fixation members pass through the channels, outside of the interference space, and can enter the portion 10 at locations outside of the interference space.

Figure 2:
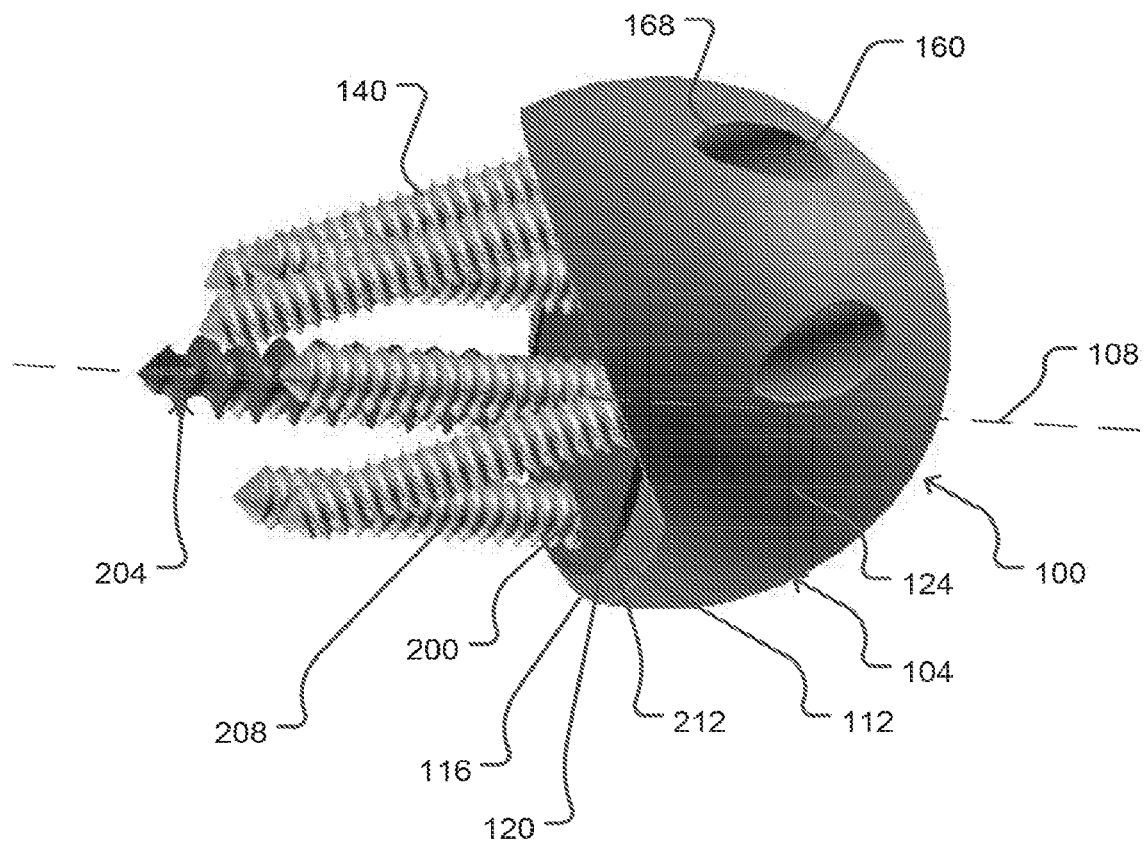
FIG. 2 is a perspective view of an embodiment of the plate and glenosphere of FIG. 1.

Referring to FIG. 2, a detailed perspective view of the glenosphere 100 and plate 200 when the plate 200 is received in the glenosphere 100 is shown. The glenosphere 100 includes a body 104. The body defines a central axis 108. The body 104 can include a variety of shapes. For example, in various embodiments, the body 104 can include a spherical shape, a substantially cylindrical shape, or any other shape allowing the glenosphere 100 to act as part of a shoulder prosthesis. The body 104 can be formed of a variety of materials, including bio-compatible materials, such as a metal, alloy, or ceramic material.

The central axis 108 of the glenosphere 100 generally defines an axis transverse to which the plate 200 is received in the glenosphere 100 (e.g., when the glenosphere 100 is positioned such that the glenosphere 100 contacts the plate 200, the plate 200 is at least partially positioned within a feature of the glenosphere 100 such as cavity 128 shown in FIGS. 3-6, etc.). For example, the glenosphere 100 may include receiving surface or an engagement member, such as an engagement member that allows for a Morse taper between the glenosphere 100 and the plate 200 that extends from the glenosphere 100 in a direction parallel or substantially parallel to the central axis 108. The central axis 108 can pass through a center or close to a center or central plane of the glenosphere 100.

The glenosphere 100 includes a first surface 112 including a first rim 116 and a second rim 120. The first rim 116 is positioned radially outward from the second rim 120, such as by being radially outward relative to the central axis 108 and/or where the central axis 108 intersects the first surface 112. In some embodiments, the first surface 112 includes material configured to contact the portion 10 of the shoulder bone. For example, the first surface 112 can include a textured surface configured to engage the portion 10 to couple the glenosphere 100 to the portion 10.

The glenosphere 100 includes a second surface 124. The second surface 124 extends from the first rim 116 of the first surface 112. For example, as shown in FIG. 2, each of the first rim 116 and the second surface 124 include an arcuate shape, such that an edge of the second surface 124 follows the arcuate shape of the first rim 116.

The second surface 124 has a convex shape. The convex shape of the second surface 124 allows the second surface 124 to engage other portions of a shoulder prosthesis system, such as a joint attached to a humerus bone (not shown). For example, the convex shape of the second surface 124 can provide the glenosphere 100 with a spherical or substantially spherical shape, in order to act as a ball in a ball-and-joint prosthesis system such that the joint can articulate about the second surface 124.

In some embodiments, as shown, e.g., in FIGS. 2-8, the glenosphere 100 can have a shape that is greater than or equal to a hemispherical shape. For example, the glenosphere 100 occupies a greater volume than to a hemisphere defined by radii extending from a center of the glenosphere 100 (the center can be defined by a point at which radii of the glenosphere 100 intersect, at which radii of a full sphere superimposed on the glenosphere 100 would intersect, etc.). By having a shape that is greater than or equal to a hemispherical shape, the glenosphere 100 can be configured to contact the baseplate 200 further away from the portion 10, providing greater clearance for the glenosphere 100 relative to the shoulder bone when the glenosphere 100 is fixated to the portion 10, and can otherwise improve the kinematics of the glenosphere 100 for the patient.

Figure 3:
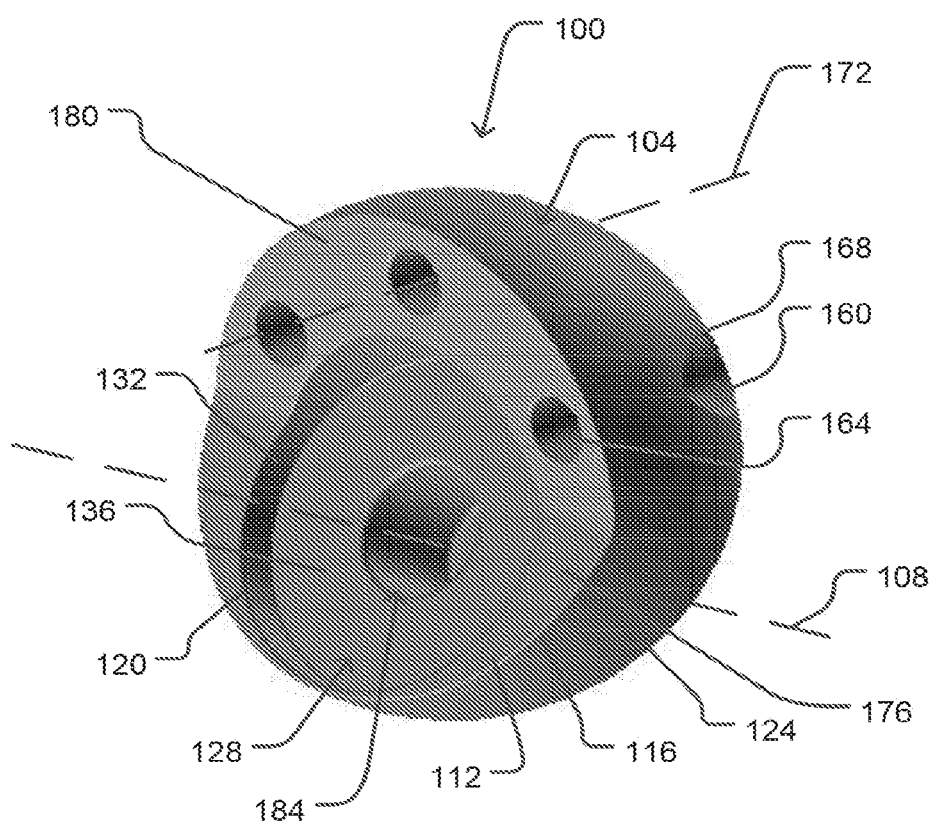
FIG. 3 is a detailed perspective view of an embodiment of the glenosphere of FIG. 1.
Figure 4:
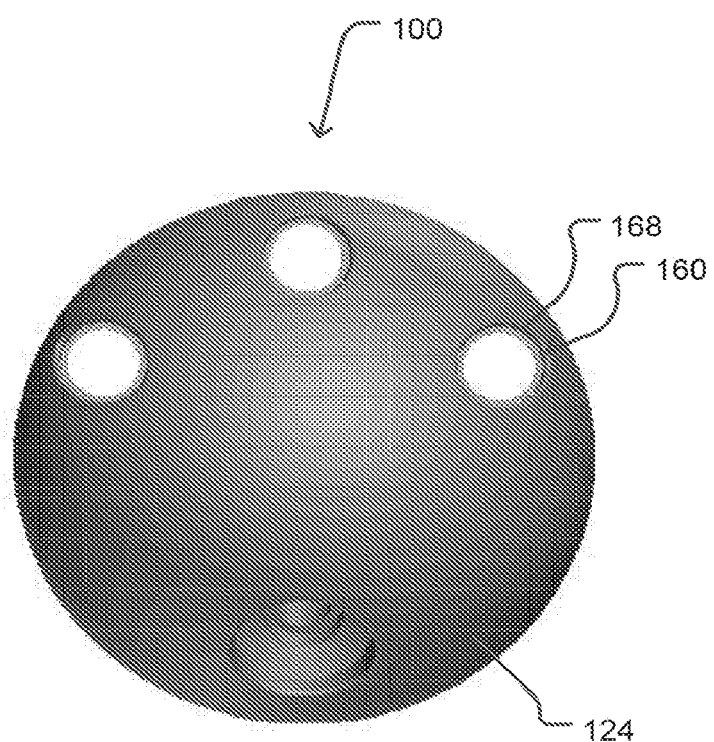
FIG. 4 is a side view transverse to a channel axis of an embodiment of the glenosphere of FIG. 1.
Figure 5:
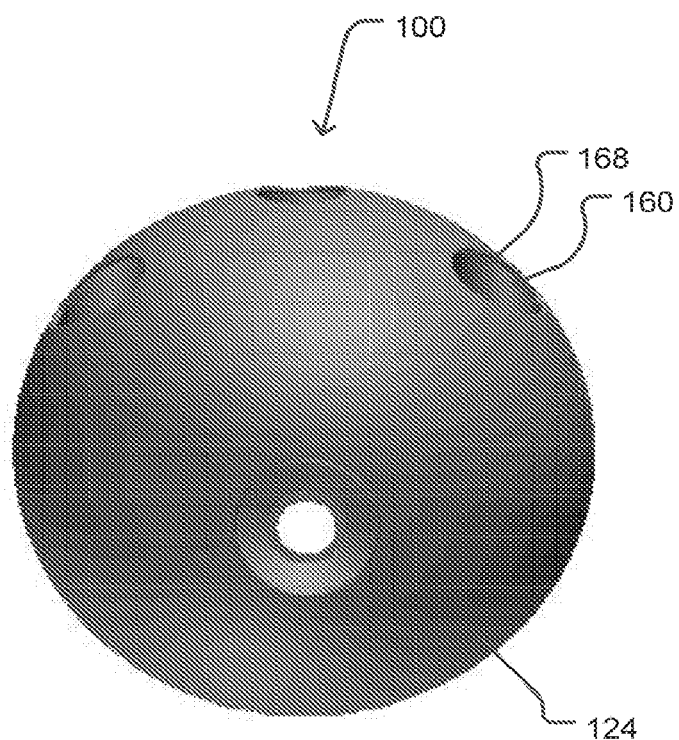
FIG. 5 is another side view transverse to a central axis of an embodiment of the glenosphere of FIG. 1.

In some embodiments, as shown, e.g., in FIG. 3, the central axis 108 is located or shifted towards an outer portion of the glenosphere 100 (e.g., towards the second surface 124, away from a plurality of channels 160 as shown in FIG. 3 and described herein) relative to an axis that would pass through the center of the glenosphere 100 (e.g., the central axis 108 is positioned between an axis that would pass through the center of the glenosphere 100 and an axis that would be tangential to the second surface 124). By having the central axis 108 located towards the outer portion of the glenosphere 100, the glenosphere 100 can have improved kinematics for the patient.

The glenosphere 100 can be configured to receive one or more glenosphere fixation members 140. The glenosphere fixation members 140 are configured to secure the glenosphere 100 to the portion 10 of the shoulder bone. The glenosphere fixation members 140 are configured to be positioned outside an interference space of the plate 200. The glenosphere fixation members 140 can include engagement features (e.g., threads on an outer surface of the glenosphere fixation members 140) or other elements allowing the glenosphere fixation members 140 to be driven through the portion 10 to be frictionally secured in the shoulder bone. The glenosphere fixation members 140 can include a variety of components, including fasteners, screws (e.g., compression screws, tapered screws), bolts, etc.

The glenosphere 100 includes a plurality of channels 160. The plurality of channels 160 extend from the first surface 112 through the body 104 to the second surface 124. Each channel 160 defines a first opening (e.g., first opening 164 shown in FIG. 3) positioned on the first surface 112, and a second opening 168 positioned on the second surface 124. The plurality of channels 160 allow for a corresponding plurality of glenosphere fixation members 140 to be received through the plurality of channels 160. The channels 160 can be configured to receive corresponding glenosphere fixation members 140 such that the glenosphere fixation members 140 can be attachable to portions of bone that are different from portions of bone at which attachment fixation members that secure an attachment structure (e.g., the plate 200) to the bone are attached to the bone.

In various embodiments, the glenosphere 100 can include various numbers of channels 160 (e.g. 1, 2, 3, 4, 5, etc.). One or more of the plurality of channels 160 can be configured to receive a glenosphere fixation member 140. For example, one or more of the plurality of channels 160 can include engagement receiving features (e.g., slots, threads located on the surface of channels 160 extending from channels 160, etc.) configured to reciprocally engage engagement features of the glenosphere fixation members 140.

In some embodiments, fewer glenosphere fixation members 140 are received in the channels 160 than the number of channels 160. For example, the glenosphere 100 can include four channels 160 configured to receive glenosphere fixation members 140. Depending on factors including the positions at which plate fixation members 208 attach the plate 200 to the bone, the shape of the interference space defined by the plate 200 (or other components such as the bone engagement member 204, the plate fixation members 208, etc.), and/or the condition of a surface of the portion 10 (e.g., a susceptibility to glenoid bone loss), three glenosphere fixation members 140 can be received in three of the four channels 160 such that the glenosphere fixation members 140 pass outside of the interference space to enter the portion 10 of the shoulder bone. Other such combinations of glenosphere fixation members 140 and channels 160 may be used.

In some embodiments, target locations on the portion 10 of the shoulder bone at which glenosphere fixation members 140 are to be secured to the portion 10 are determined based on at least one of imaging data of the portion 10 and a bone loss model of the portion 10. The glenosphere 100 can be configured or designed (e.g., designed in a custom design process to match a particular portion 10 and/or plate 200) and manufactured so that glenosphere fixation members 140 received through the channels 160 can be secured to the portion 10 at the target locations. The glenosphere 100 can be oriented (e.g., positioned and/or rotated) so that glenosphere fixation members 140 received through the channels 160 can be secured to the portion 10 at the target locations. The glenosphere 100 can be configured such that the channels 160 have channel axes 172 that do not intersect plate fixation members 208 received in the plate 200 based on a geometry of the plate 200 and the plate fixation members 208.

In some embodiments, the channels 160 are tapered (e.g., a cross-sectional area of a channel 160 changes from first opening 164 to second opening 168). For example, the channels 160 can be tapered to decrease in cross-sectional area from the second opening 168 to the first opening 164, which can facilitate orienting the glenosphere 100 by using the first opening 164 as a focus point, and which can improve the frictional fit between the channel 160 and a glenosphere fixation member 140.

The plate 200 can include a bone engagement member 204. The bone engagement member 204 extends from the plate 200. In some embodiments, the bone engagement member 204 extends along the central axis of the glenosphere 100 when the plate 200 is received in the glenosphere 100. In some embodiments, the bone engagement member 204 is offset and/or skew relative to the central axis of the glenosphere 100 when the plate is received in the glenosphere 100. In some embodiments, the bone engagement member 204 is integrally formed with the plate 200. In other embodiments, the bone engagement member 204 can be separate from the plate 200 and received in an opening of the plate 200.

The bone engagement member 204 can be configured to secure the plate 200 to the portion 10 of the shoulder bone. The bone engagement member 204 can include engagement features (e.g., threads located on an outer surface of the bone engagement member 204) or other elements allowing the bone engagement member 204 to be driven through a surface of the portion 10 to be frictionally secured in the shoulder bone.

The plate 200 can be configured to receive plate fixation members 208. The plate fixation members 208 can be similar or identical to the glenosphere fixation members 140. The plate fixation members 208 can extend in a direction parallel to the bone engagement member 204 from the plate 200. The plate fixation members 208 can extend in directions that are offset and/or skew relative to the bone engagement member 204. In some embodiments, the plate fixation members 208 are oriented at an offset angle relative to the central axis 108 when the plate 200 is received in the cavity 128 of the glenosphere 100. In various embodiments, the plate 200 can be configured to receive various numbers of plate fixation members 208 (e.g. 1, 2, 3, 4, 5, etc.).

In some embodiments, the plate fixation members 208 and glenosphere fixation members 140 can include engagement features having opposite directions (e.g., threads located on outer surfaces of the plate fixation members 208 and glenosphere fixation members 140 having opposite threadforms), such that forces applied to the plate 200 and the glenosphere 100 can be distributed via the plate 200 or the glenosphere 100 depending on the direction of the forces.

In some embodiments, the plate 200 can define an interference space. The interference space indicates a region in space in which fixation members used to secure the glenosphere 100 to the portion 10 (e.g., glenosphere fixation members 140), do not pass through. As such, the glenosphere 100 can be oriented so that the glenosphere 100 does not interfere with the fixation of the plate 200 to the portion 10. Instead, the fixation of the glenosphere 100 to the portion 10 is augmented by the glenosphere fixation members 140, which strengthens the connection between the plate 200 and glenosphere 100 to the portion 10, helping to mitigate bone loss damage. In some embodiments, the interference space extends to a surface of the portion 10. In some embodiments, such as if a plate is formed as a plurality of plates, the interference space can include a plurality of regions, such as a plurality of discrete and/or overlapping regions corresponding to one or more of the plurality of plates.

In some embodiments, the plate fixation members 208 of the plate 200 can define the interference space. For example, the interference space can include a volume occupied by the plate fixation members 208, such as a volume exactly occupied by the plate fixation members 208, a volume substantially occupied by the plate fixation members 208, a volume exactly occupied by the plate fixation members 208 supplemented by a boundary region (e.g., a boundary region consisting of a volume of space extending outward from the plate fixation members 208, such as by a fractional distance relative to a dimension of the plate fixation members 208), etc. The interference space can also be at least partially defined by the bone engagement member 204 of the plate 200. In some embodiments, the interference space can be a volume or region within the bone to which the plate 200 is coupled that is occupied by the plate fixation members In some embodiments, the interference space is defined to include at least a portion of an interior volume between the plate fixation members 208, such that the glenosphere 100 can be oriented such that any glenosphere fixation members 140 are positioned outside of multiple plate fixation members 208. In other embodiments, the interference space is defined to exclude at least a portion of an interior volume between the plate fixation members 208, such that the glenosphere 100 can be oriented such that at least one glenosphere fixation member 140 can be positioned at least partially between at least two plate fixation members 208.

Referring now to FIGS. 3-6, the glenosphere 100 is shown isolated from the plate 200 and any fixation members. The glenosphere 100 includes a cavity 128. The cavity 128 extends into the body from the first surface 112. The cavity is defined by a cavity wall 132 that extends from the second rim 120 of the first surface 112 in a direction substantially parallel to the central axis 108 to a cavity surface 136, and by the cavity surface 136.

Figure 6:
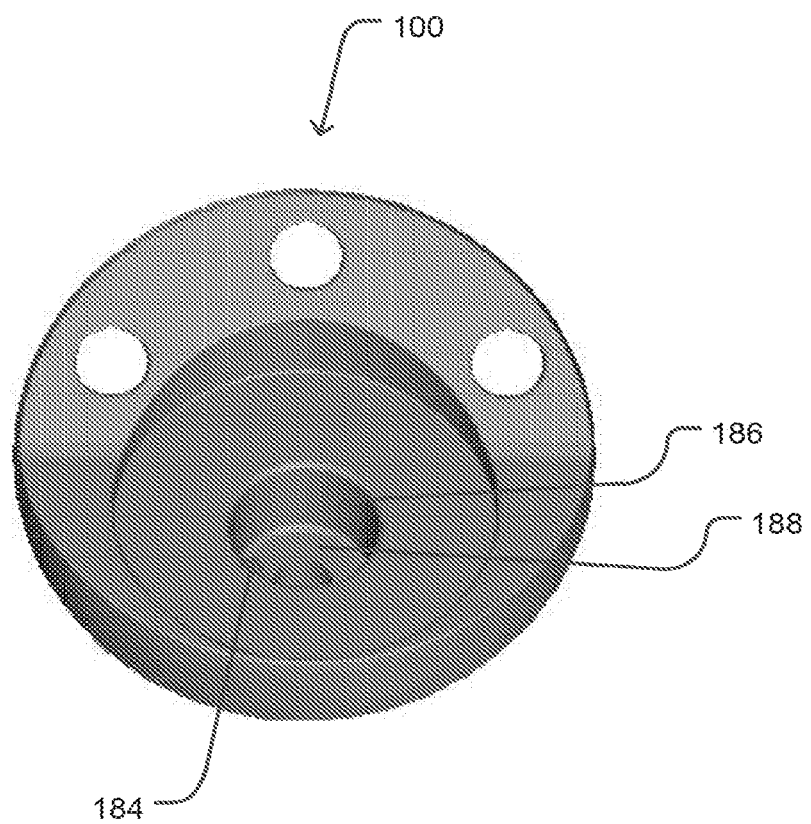
FIG. 6 is another side view facing a cavity of an embodiment of the glenosphere of FIG. 1.
Figure 10:
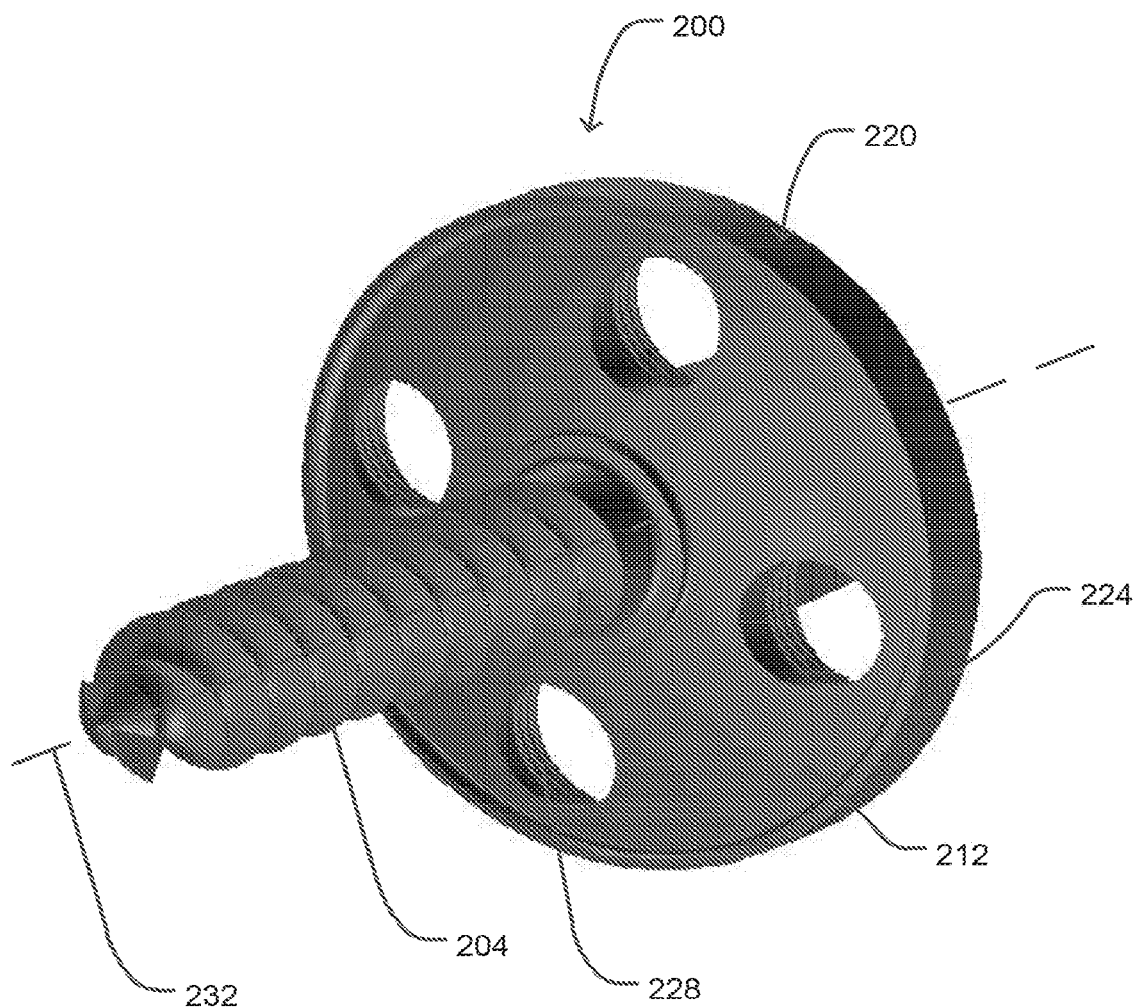
FIG. 10 is a detailed perspective view of an embodiment of the plate of FIG. 1.

The cavity 128 is configured to receive the plate 200 such that the cavity surface 136 contacts a surface of the plate 200 (e.g., second plate surface 216 shown in FIG. 10, etc.). For example, the cavity 128 can include a shape that matches at least a part of a shape of the second plate surface 216 of the plate 200. The cavity 128 can include a circumference that corresponds to a circumference of the plate surface 216. As shown in FIGS. 3 and 6, the cavity 128 includes a generally circular shape configured to match a shape of the plate 200, such that the cavity wall 132 can engage an outer edge of the plate 200.

As shown in FIG. 3, the cavity 128 is positioned such that the central axis 108 defined by the body 104 passes through the cavity 128 transverse (e.g., perpendicular) to the cavity surface 136. As such, the plate 200 may be received in the cavity 128 such that a bone engagement member of the plate 200 is positioned along the central axis 108.

In some embodiments, the cavity surface 136 of the cavity 128 includes frictional elements configured to frictionally engage the second plate surface 216 of the plate 200. For example, the cavity surface 136 can include a textured surface that enhances frictional engagement between the cavity 128 and the plate 200. The frictional engagement between the surfaces can help distribute forces applied to the glenosphere 100 to the plate 200 in order to distribute the forces transferred to the portion 10 of the shoulder bone. In some embodiments, the cavity 128 includes locking elements (e.g., hooks, latches, flanges, etc.) configured to engage a corresponding locking element (e.g., hooks, latches, flanges, etc.) of the plate 200. For example, orienting the glenosphere 100 so that the cavity 128 receives the plate 200 can include aligning the locking elements and pressing together the glenosphere 100 to the plate 200 or rotating the glenosphere 100 relative to the plate 200 to lock the glenosphere 100 to the plate 200.

In some embodiments, the first surface 112 includes a first region 176 substantially perpendicular to the central axis 108 and a second region 180 disposed at an angle to the first region 176. For example, the second region 180 can form an obtuse angle with the first region 176. A length of the cavity wall 132 between the cavity surface 136 and the first surface 112 can increase continuously between the first region 176 and the second region 180, such that the cavity surface 136 maintains a flat or planar shape adjacent to both the first region 176 and the second region 180. A first portion of the cavity wall 132 extends from a portion of the second rim 120 adjacent to the first region 176, and a second portion of the cavity wall 132 extends from a second portion of the second rim 120 adjacent to the second region 180.

In some embodiments, one or more of the first openings 164 of the plurality of channels 160 are positioned on the second region 180. As shown in FIG. 3, each of the first openings 164 of the plurality of channels 160 are positioned on the second region 180. Positioning the first openings 164 on the second region 180 can facilitate orienting the glenosphere 100 such that glenosphere fixation members (e.g., glenosphere fixation members 140 shown in FIG. 2, etc.) can be positioned to pass through the plurality of channels 160 outside of an interference space defined by the plate 200. In some embodiments, at least one of the first openings 164 is positioned on the first region 176 so as to orient at least one glenosphere fixation member 140 at an angle to other glenosphere fixation members 140.

The plurality of channels 160 define a plurality of channel axes 172 passing through the plurality of channels 160. As shown in FIG. 3, the channel axes 172 are positioned perpendicular to the first surface 112. The plurality of channels extend from a first opening 164 on the first surface 112 to a second opening 168 on the second surface 124. As shown in FIGS. 3-6, the channel axes 172 can be oriented parallel to one another. In various embodiments, the orientation of the plurality of channels 160 and thus of the channel axes can be varied in order to alter the direction that glenosphere fixation members 140 passing through the plurality of channel axes 172 extend. For example, while FIG. 3 shows the channels 160 oriented perpendicular to the first surface 112 (e.g., the channels axes 172 are perpendicular to the first surface 112), in other embodiments, the channels 160 can be oriented at an acute angle to the first surface 112. For example, orienting a channel 160 at an acute angle to the first surface 112, so that a distance between the channel axis 172 of the channel 160 and the central axis 108 decreases as the axes 108, 172 extend away from the glenosphere 100 (e.g., extend towards the portion 10 of the shoulder bone, extend in a direction substantially perpendicular to first surface 112 or second surface 116, etc.), allows the glenosphere fixation members 140 to be secured to the portion 10 at locations that are relatively close to where the plate 200 is secured to the portion 10, which can reduce the surface area of the portion 10 required for the shoulder prosthesis. In another example, orienting a channel 160 at an acute angle to the first surface 112, so that a distance between the channel axis 172 of the channel 160 and the central axis 108 increases as the axes 108, 172 extend away from the glenosphere 100 (e.g., extend towards the portion 10 of the shoulder bone, extend in a direction substantially perpendicular to first surface 112 or second surface 116, etc.), allows the glenosphere fixation members 140 to be secured to the portion 10 at locations that are relatively close to where the plate 200 is secured to the portion 10, which can reduce the stress on the surface of portion 10 required for the shoulder prosthesis. In some embodiments, at least one the plurality of channels 160 is oriented perpendicular to the first surface 112, and at least one of the plurality of channels 160 is oriented at an acute angle to the first surface 112.

In embodiments in which the glenosphere 100 includes a first surface 112 having a first region 176 and a second region 180 disposed at an angle to the first region 176, the channel axes 172, which are perpendicular to the first surface 112 and the second region 180, are oriented at an angle to the central axis 108. For example, if the second region 180 is disposed at an obtuse angle relative to the first region 176, the channel axes 172 will be oriented at an acute angle relative to the central axis 108. In this manner, the glenosphere fixation members 140 received through the plurality of channels 160 and positioned along the channel axes 172 can be positioned outside of the interference space of the plate 200 yet engage a portion of the portion 10 proximate to where plate engagement members of the plate engage the portion 10.

Figure 11:
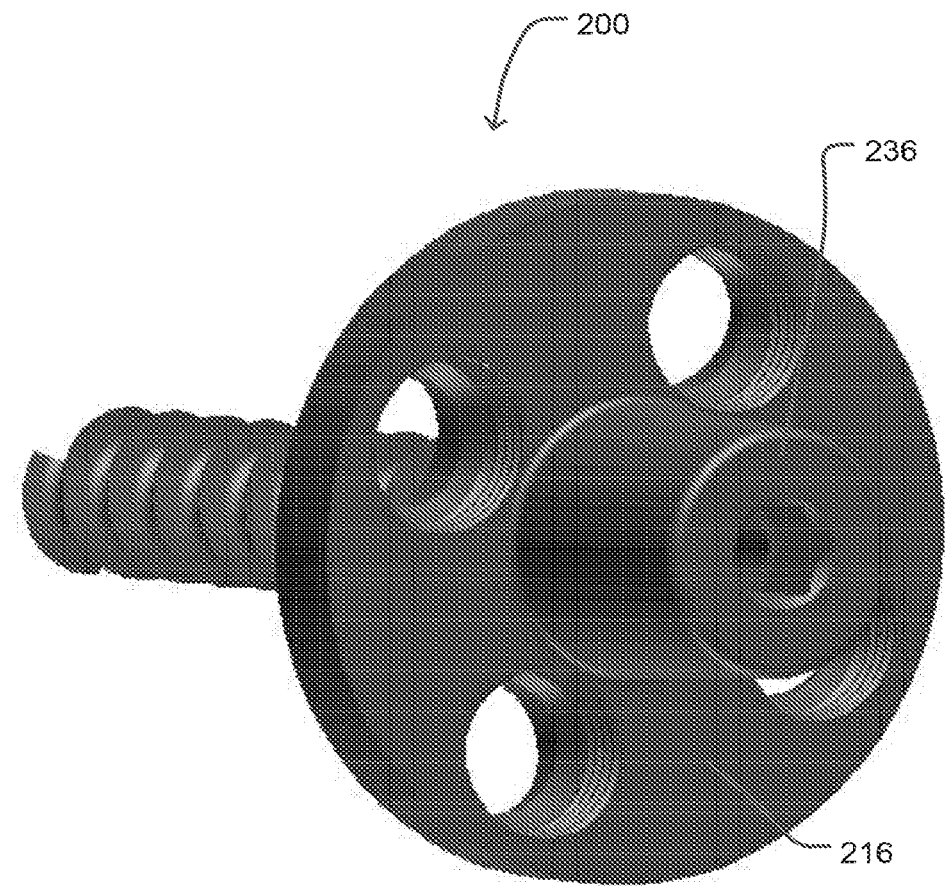
FIG. 11 is another perspective view of an embodiment of the plate of FIG. 1.

Referring further to FIGS. 3 and 6, in some embodiments, the cavity 128 includes an inner cavity portion 184. The inner cavity portion 184 can include a second cavity wall 186 and a second cavity surface 188. The inner cavity portion 184 can be configured to receive a component extending from a surface of a plate (e.g., plate 200). For example, the inner cavity portion 184 can act as an engagement member for engaging a corresponding engagement member of the plate 200 (e.g., engagement member 236 as shown in FIG. 11, etc.). For example, the inner cavity portion 184 can be or include a first engagement member configured to engage a second engagement member 236 of the plate 200. In some embodiments, the inner cavity portion 184 is configured to form a Morse taper with the engagement member 236 of the plate 200. In some embodiments, the inner cavity portion 184 and engagement member 236 include complementary engagement elements (e.g., hooks, latches, flanges, threaded couplings, etc.) for securing the glenosphere 100 to the plate 200.

Figure 7:
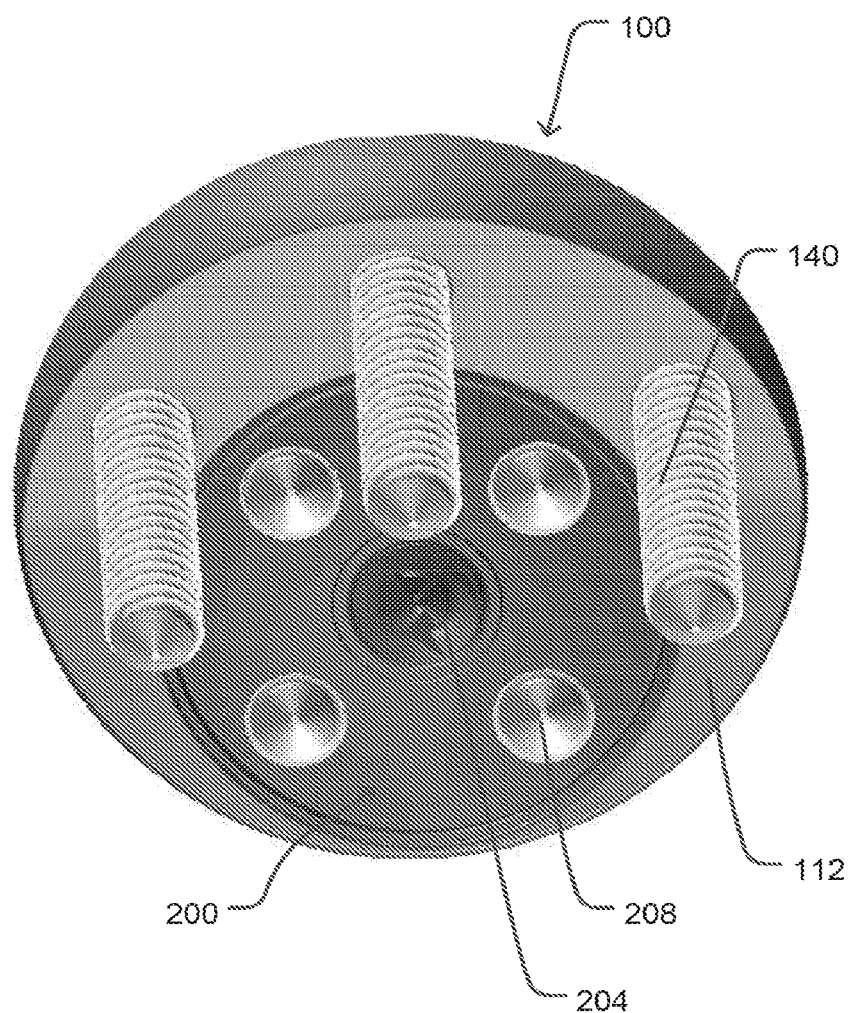
FIG. 7 is a side view of an embodiment of the plate and glenosphere of FIG. 1 with fixation members received in each of the plate and glenosphere.
Figure 8:
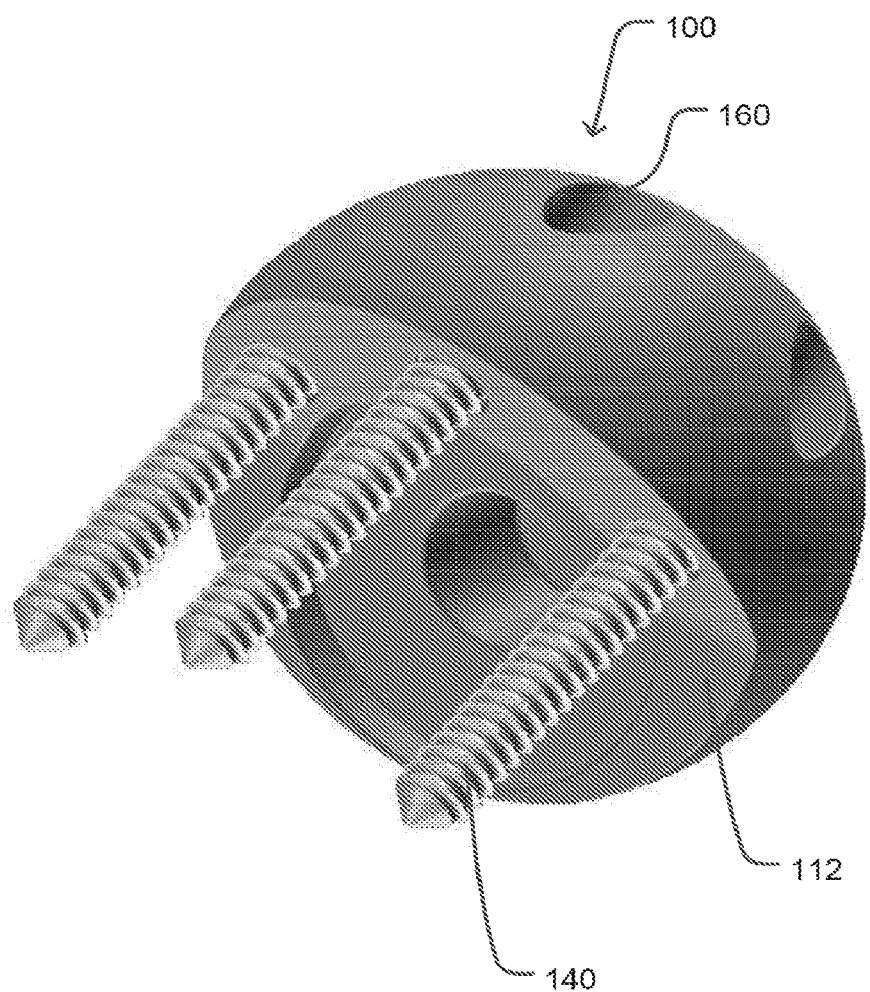
FIG. 8 is a perspective view of an embodiment of the glenosphere of FIG. 1 with fixation members received in the plurality of channels of the glenosphere.
Figure 9:
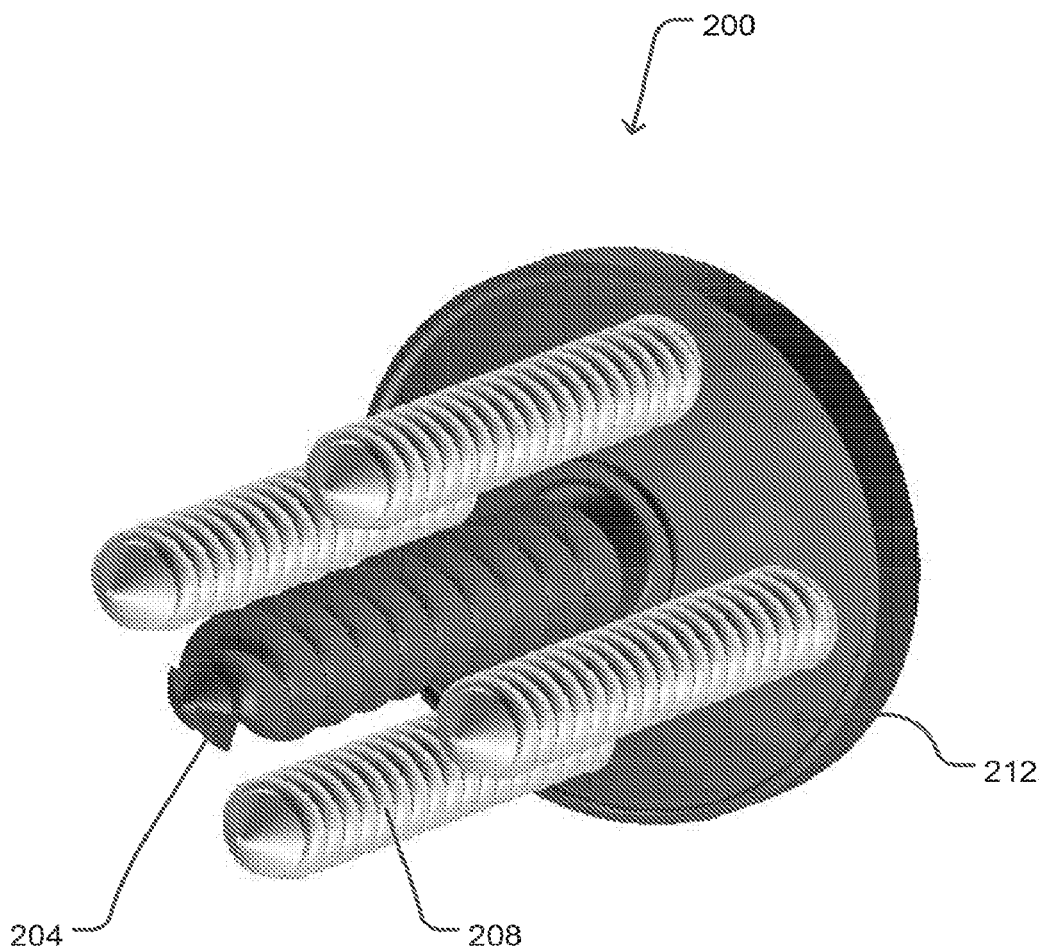
FIG. 9 is a perspective view of an embodiment of the plate of FIG. 1 with fixation members received in the plate.

Referring now to FIGS. 7-9, the glenosphere 100 and plate 200 are shown in various configurations with fixation members. In FIG. 7, an end view of the glenosphere 100 and plate 200 with fixation members is shown. The plurality of glenosphere fixation members 140 are received in the plurality of channels 160 of the glenosphere 100. The plurality of plate fixation members 208 extend from the plate 200. In FIG. 8, a perspective view of the glenosphere 100 with glenosphere fixation members 140 is shown. In FIG. 9, a perspective view of the plate 200 with plate fixation members 208 is shown.

In FIG. 7, the glenosphere 100 and plate 200 are shown looking down the central axis (e.g., central axis 108 shown in FIG. 8) of the glenosphere 100, and the bone engagement member 204 of the plate 200 is oriented along the central axis 108. In other words, an axis of the bone engagement member 204 and the plate 200 is coaxial with the central axis 108 of the glenosphere 100. As further shown in FIG. 7, the plurality of plate fixation members 208 are oriented in the same direction as the bone engagement member 204, such that they are parallel to and offset from the central axis 108 and the bone engagement member 204.

The plurality of glenosphere fixation members 140 can extend at an angle relative to the central axis 108 and the bone engagement member 204 and plate fixation members 208. For example, as shown in FIGS. 7 and 8, the first surface 112 of the glenosphere 100 includes a first region 176 and a second region 180 oriented at an obtuse angle relative to the first region 176. The plurality of first openings 164 of the plurality of channels 160 are positioned in the second region 180 of the first surface 112, such that the plurality of glenosphere fixation members 140 extend out from the glenosphere 100 at an angle to the central axis 108, and thus at an angle relative to components extending from the plate 200 when the plate 200 is received in the glenosphere 100. The glenosphere fixation members 140 are configured to extend out of the first openings 164, past an interference space of the plate 200 when the plate 200 is received in the glenosphere 100, to secure the glenosphere 100 to the portion 10 of the shoulder bone.

Referring further to FIG. 9, the plate fixation members 208 extend from the plate 200 in the same direction as the bone engagement member 204. The plate fixation members 208 can have a variety of lengths. For example, the plate fixation members 208 can have a similar length to the bone engagement member 204, such as by having a length that is slightly less than the length of the bone engagement member 204. The length of the plate fixation members 208 can be selected based on imaging data indicating compatibility of the portion 10 of the shoulder bone for receiving an engagement member.

Figure 12:
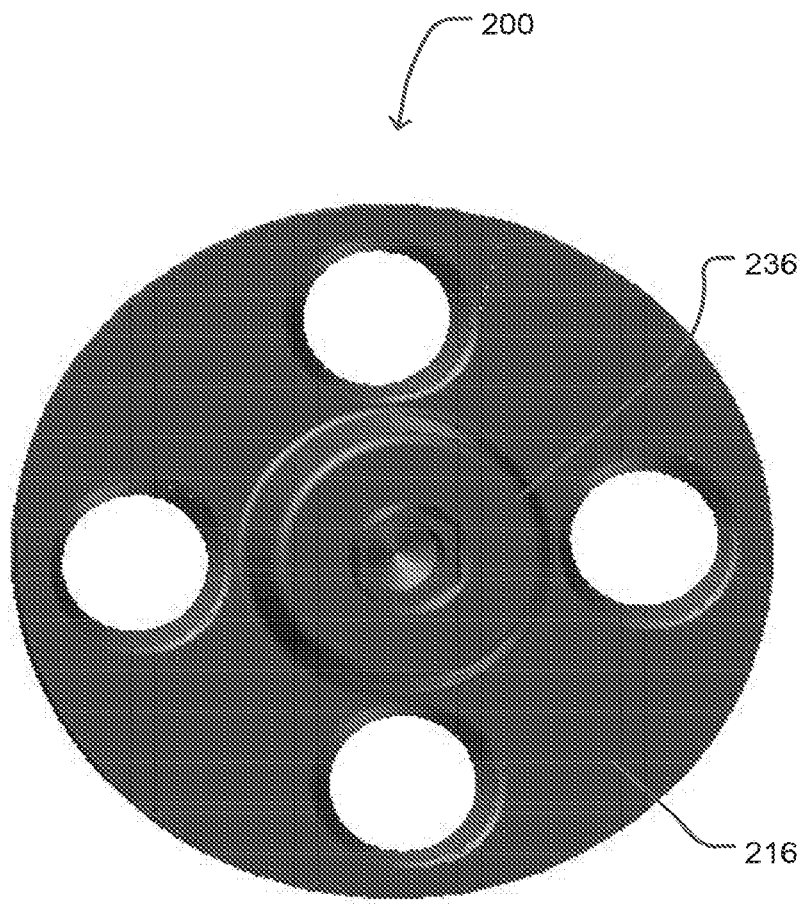
FIG. 12 is an end view of an embodiment of the plate of FIG. 1.

Referring now to FIGS. 10-12, the plate 200 is shown isolated from the glenosphere 100 and any fixation members. The plate 200 includes a first plate surface 212 on a side of the plate 200 from which the bone engagement member 204 extends, and a second plate surface 216 on an opposite side of the plate 200 from the first plate surface 212. A plate body 220 is disposed between the first plate surface 212 and the second plate surface 216. The plate body 220 includes a plate wall 224 along an outer portion (e.g., circumference) of the plate body 220. In some embodiments, the plate body 220 and plate wall 224 are configured to be received in a cavity of a glenosphere such that the plate wall 224 is positioned flush against the a wall of the cavity (e.g., cavity 128, cavity wall 132 of glenosphere 100 as shown in FIG. 3, etc.). The second plate surface 216 of the plate 200 can be positioned flush against a surface of the cavity 128 (e.g., cavity surface 136 as shown in FIG. 3, etc.).

The plate 200 includes a plurality of plate channels 228. Each plate channel 228 extends from an opening on the first surface 212 to an opening on the second plate surface 216. The plurality of plate channels 228 are configured to receive the plurality of plate fixation members (e.g., plate fixation members 208 shown in FIG. 9, etc.). The plurality of plate channels 228 can include engagement receiving surfaces (e.g., threaded surfaces) configured to receive and engage with engagement features (e.g., threads) of the plate fixation members 208 in order to frictionally couple the plate 200 to the plate fixation members 208 as the plate 200 is secured to the portion 10 of the shoulder bone. The plurality of plate channels 228 can be oriented transverse (e.g., perpendicular) to a plate axis 232 along with the bone engagement member 204 is oriented, such that the plate fixation members 208 can be oriented parallel to the bone engagement member 204 when the plate fixation members are received through the plurality of plate channels 228. In various embodiments, the plurality of plate channels 228 can be oriented at various angles relative to the plate axis 232, and can be oriented at heterogeneous angles relative to one another. For example, each of the plurality of plate channels 228 can be oriented at an angle offset to the plate axis 232. Each of the plurality of plate channels 228 can be oriented at an angle offset to the central axis 108 when the plate 200 is received in the cavity 128 of the glenosphere 100.

As shown in FIGS. 10-12, the bone engagement member 204 is integrally formed with the plate 200. In some embodiments, the plate 200 can include a receiving surface configured to receive the bone engagement member 204.

In some embodiments, as shown in FIGS. 11 and 12, the plate 200 includes an engagement member 236 configured to engage the plate 200 to a glenosphere 100 such that the plate 200 can be secured and received in a cavity of the glenosphere 100 (e.g., by engaging inner cavity portion 184 of cavity 128 of glenosphere 100 as shown in FIG. 6, etc.). For example, the glenosphere 100 and plate 200 can be secured to one another by engaging the engagement member 236 and the cavity 128 (e.g., by forming a Morse taper between the inner cavity portion 184 of the cavity 128 and the engagement member 236). The engagement member 236 can extend from the second plate surface 216 of the plate 200 in an opposite direction as the bone engagement member 204. For example, the engagement member 236 can be oriented along the plate axis 232 such that the bone engagement member 204 and the engagement member 236 are coaxial with a central axis (e.g., central axis 108 shown in FIG. 3, etc.) of the glenosphere 100 when the plate 200 is received in the glenosphere 100.

In some embodiments, the plurality of channels 160 include markings configured to facilitate orienting the glenosphere 100 when receiving the plate 200 such that glenosphere fixation members 140 passed through the glenosphere 100 will be positioned outside of the interference space. For example, the markings can be positioned parallel to the channel axes 172 passing through the channels 160, such that a line of sight following the markings can indicate an intersection with the interference space of the plate 200. The markings can include fluorescent material or other material configured to visually aid orientation of the glenosphere 100.

In some embodiments, channel guides having similar form factors to the plurality of glenosphere fixation members 140 can be used to facilitate orienting the glenosphere 100. For example, the guides can be inserted through the plurality of channels 160 in a similar manner as the glenosphere fixation members 140, in order to determine whether the glenosphere fixation members 140 would intersect or pass outside of the interference space of the plate 200. The channel guides can be removably inserted in the plurality of channels 160 so as to facilitate quick orientation of the glenosphere 100 prior to securing of the glenosphere 100 using the glenosphere fixation members 140.

Figure 13:
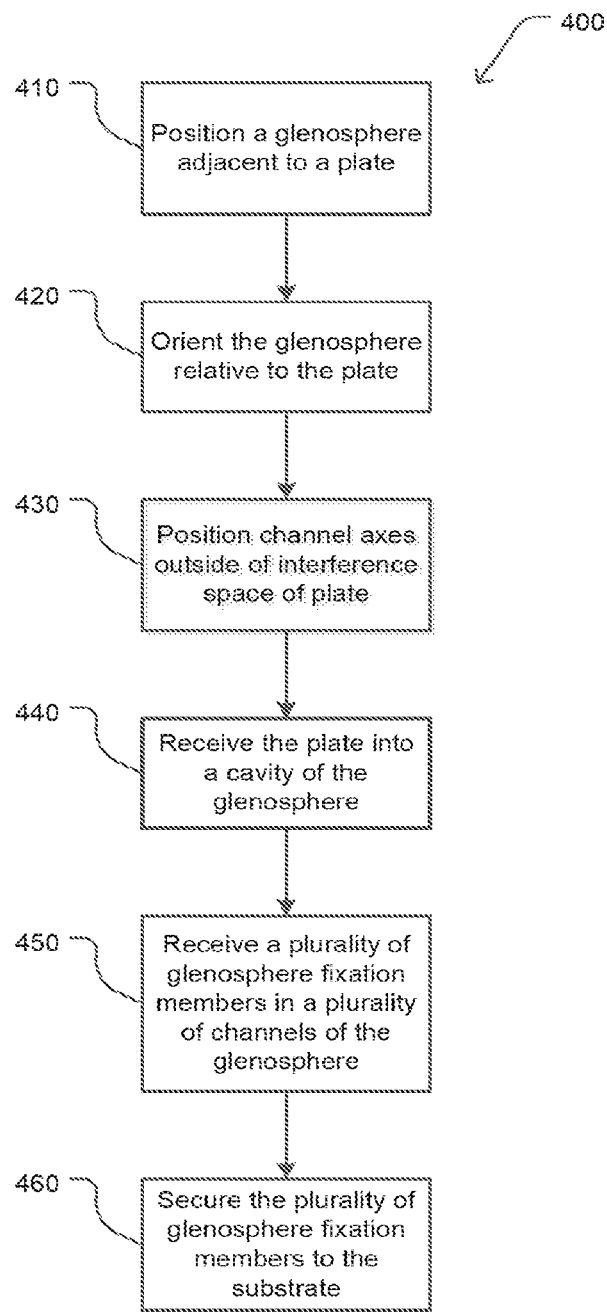
FIG. 13 is a block diagram of an embodiment of a method of securing a glenosphere to a portion of a shoulder bone to augment fixation of the glenosphere.

Referring now to FIG. 13, a block diagram of a method 400 of securing a glenosphere to a portion of a shoulder bone and to a plate fixated to the portion of the shoulder bone, such as a method that is performed as part of a shoulder arthroplasty, is shown. The method 400 can be implemented using any of the devices and systems disclosed herein, including the glenosphere 100 and plate 200 described with regards to FIGS. 1-12. A variety of actors can perform the method 400, including but not limited to a medical care professional (e.g., doctor, nurse), etc.

At 410, a glenosphere is positioned adjacent to a plate. The plate is fixated to a portion of a shoulder bone. The glenosphere includes a body defining a central axis passing through the body. The glenosphere includes a first surface including a first rim and a second rim, and a second surface extending from the first rim. The second surface has a convex shape. The glenosphere includes a cavity extending into the body from the first surface. The cavity is configured to receive the plate. The glenosphere includes a plurality of channels extending from the first surface through the body to the second surface. Each channel defines a first opening positioned on the first surface between the first rim and the second rim, defines a second opening positioned on the second surface, and defines a channel axis passing through the channel. Positioning the glenosphere can include holding the glenosphere adjacent to the plate, such as within a distance of the plate such that components of the plate are visible through the channels of the glenosphere. For example, a surgeon or other medical professional can position the glenosphere adjacent to the plate, so that the surgeon can manipulate the glenosphere in relation to the plate.

At 420, the glenosphere is oriented relative to the plate. For example, the glenosphere can be oriented such that a central axis of the glenosphere is coaxial with a plate axis of the plate. In some embodiments, the plate is already secured to the portion of the shoulder bone, and thus the glenosphere can be oriented relative to a fixed plate and fixed plate axis of the plate. The glenosphere can be oriented such that the glenosphere will be in an anatomic position, allowing for a natural range of motion when the shoulder arthroplasty is complete. In some embodiments, the glenosphere can be oriented off-axis or otherwise offset from an anatomic position, allowing for a different range of motion. For example, a surgeon or other medical professional can orient the glenosphere relative to the plate.

At 430, the channel axes of the glenosphere are positioned outside of an interference space of the plate. The interference space can be defined by plate fixation members and/or a bone engagement member of the plate. The interference space can include an exact volume of the plate fixation members and/or bone engagement member, or can include a volume lesser or greater than these components. Positioning the channel axes outside of the interference space facilitates positioning glenosphere fixation members such that the glenosphere fixation members do not collide with the plate fixation members or the bone engagement member. The interference space can be determined visually, by using marking guides, or by a combination thereof. For example, a surgeon or other medical professional can determine an extent of the interference space, and position the glenosphere—and thus the channels axes which are fixed relative to the glenosphere—such that the channel axes are positioned outside of the interference space.

In some embodiments, positioning the channel axes includes positioning marking guides in the plurality of channels to align the plurality of channels. For example, the marking guides may indicate a direction of the channel axes. In some embodiments, positioning the channel axes includes removably receiving channel guides in the plurality of channels. The channel guides can include a form factor similar or identical to glenosphere fixation members. For example, the channel guides can be received in the plurality of channels in a similar orientation as the glenosphere fixation members would be received, and the orientation of the glenosphere can be adjusted until the channel guides (and thus the channel axes) are positioned outside of the interference space. For example, orienting the glenosphere can include receiving a plurality of channel guides in the plurality of channels and modifying the orientation of the glenosphere until each of the channel guides is positioned outside of the interference space. A surgeon or other medical professional can insert the channel guides through the plurality of channels and modify the orientation of the glenosphere based on whether each of the channel guides are positioned outside of the interference space.

In some embodiments, positioning the channel axes includes orienting the glenosphere such that the channel axes are positioned outside the interference space (e.g., the channel axes do not intersect the interference space). In some embodiments, positioning the channel axes includes orienting the glenosphere such that a volume about each respective channel axis is positioned outside of the interference space (e.g., a volume about each respective channel axis does not intersect the interference space). The volume about each respective channel axis can be an extrapolation of the respective channels, such as a cylindrical volume extending from the openings of the channels.

In some embodiments, positioning the channel axes includes positioning the channel axes based on an offset between a first position of the glenosphere before the plate is received in the glenosphere, and a second position of the glenosphere after the plate is received in the glenosphere. For example, in the first position, the glenosphere may be positioned and oriented such that the channel axes intersect the interference space, yet as the plate is received in the glenosphere (such as by decreasing a distance between the glenosphere and the plate by moving the glenosphere towards the portion of the shoulder bone and the plate along the plate axis of the plate), the channel axes become positioned outside of the interference space. In some embodiments, channel guides are used that have a shape and a guide length that is offset relative to a length of a glenosphere fixation member, such as an offset based on a dimension of the cavity of the glenosphere, such that the channel guides match the position of the channel axes when the plate is received in the cavity of the glenosphere.

In some embodiments, orienting the glenosphere includes orienting the channels such that the glenosphere fixation members received in the channels are attached to a portion of the bone that is different from a portion of the bone at which plate fixation members are attached to the bone. In some embodiments, the interference space is defined by regions of the bone occupied by the plate fixation members to reduce failure of the attachment of the plate to the bone.

At 440, the plate is received into the cavity of the glenosphere. For example, the glenosphere can be pressed against the plate such that the plate fits into the cavity. The channel axes will continue to be positioned outside of the interference space of the plate. In some embodiments, receiving the plate includes engaging a first engagement member of the glenosphere with a second engagement member of the plate, such as for forming a Morse taper between the glenosphere and the plate. In some embodiments, a cavity wall of the cavity is configured to be positioned flush against a plate wall of the plate, and a cavity surface of the cavity is configured to be positioned flush against a surface of the plate when the plate is received in the cavity. For example, a surgeon, having positioned and oriented the glenosphere such that the central axis of the glenosphere is coaxial with the plate axis of the plate and the channel axes are positioned outside of the interference space, can shift the glenosphere towards the plate and the portion of the shoulder bone so that the plate fits into the cavity.

At 450, a plurality of glenosphere fixation members are received in the plurality of channels. Because the glenosphere has been oriented such that the channel axes (or volumes about the channel axes) are positioned outside of the interference space of the plate, the glenosphere fixation members when received in the plurality of channels will also be positioned outside of the interference space. A surgeon can place the glenosphere fixation members into the channels so that the glenosphere fixation members are positioned outside of the interference space, and so that the glenosphere fixation members contact the portion of the shoulder bone to which they will be secured.

At 460, the plurality of glenosphere fixation members are secured to the portion of the shoulder bone in order to augment fixation of the glenosphere to the portion of the shoulder bone. The glenosphere fixation members can include engagement features (e.g., threads or other frictional elements) configured to engage the portion of the shoulder bone. Securing the glenosphere fixation members to the portion of the shoulder bone thus allows for forces transmitted through the glenosphere and plate to the portion of the shoulder bone to be transmitted to positions other than the positions where the bone engagement member and/or plate fixation members are secured to the portion of the shoulder bone, helping to distribute stresses on the portion of the shoulder bone and mitigate bone loss. For example, a surgeon can use a driver, drill, or other tool to drive the glenosphere fixation members into the portion of the shoulder bone to secure the glenosphere to the portion of the shoulder bone.

In some embodiments, the method includes positioning one or more of the plate and the glenosphere based on imaging data regarding the patient. The imaging data can identify preferred positions for the plate and/or glenosphere in order to provide the shoulder prosthesis system in an anatomic position, to mitigate bone loss or minimize the effects of bone loss, etc. The imaging data can indicate target positions for fixation members to be secured to the portion of the shoulder bone.

In some embodiments, a method of securing a glenosphere to a portion of a shoulder bone and to a plate fixed to the portion of the shoulder bone includes positioning the glenosphere adjacent to the plate. The glenosphere can include a body defining a central axis passing through the body, a first surface including a first rim and a second rim, a second surface extending from the first rim of the first surface, the second surface having a convex shape, a cavity extending into the body from the first surface, the cavity configured to receive the plate, and a plurality of channels extending from the first surface through the body to the second surface. Each channel can define a first opening positioned on the first surface between the first rim and the second rim. Each channel can define a second opening positioned on the second surface. Each channel can be configured to receive a bone fixation member configured to secure the glenosphere to the bone. The method can include orienting the glenosphere relative to the plate such that each glenosphere fixation member received by the channels is attachable to a portion of bone that is different from a portion of bone at which plate fixation members attach the plate to the bone. The method can include orienting the glenosphere relative to the plate such that each glenosphere fixation members received by the channels is attachable to a portion of bone outside of an interference space defined by regions of bone occupied by plate fixation members that attach the plate to the bone. The method can include receiving the plate into the cavity. The method can include receiving a plurality of glenosphere fixation members in the plurality of channels via the plurality of second openings such that the plurality of glenosphere fixation members are positioned outside of the interference space and contact the portion of the shoulder bone. The method can include securing the plurality of glenosphere fixation members to the portion of the shoulder bone. In some embodiments, orienting the glenosphere includes receiving a plurality of channel guides in the plurality of channels and modifying the orientation of the glenosphere until each of the channel guides is positioned outside of the interference space.

In some embodiments, a glenosphere for use in a shoulder prosthesis includes a body, a first surface, a second articulating surface, and a plurality of channels. The body includes a baseplate engagement region, and defines a center of rotation. The baseplate engagement region includes an engager defining an engagement axis offset from the center of rotation. The first surface is outward from the baseplate engagement region and includes a first rim. The second articulating surface extends from the first rim of the first surface. The second surface has a convex shape. The plurality of channels extend from the first surface through the body to the second surface. Each channel of the plurality of channels defines a first opening positioned on a same side of the first surface relative to a plane including the engagement axis. Each channel defines a channel axis extending through the corresponding channel. Each channel axis is radially outward from the engagement axis and spaced from the baseplate engagement region. Each channel is configured to receive a bone fixation member configured to secure the glenosphere to the bone.

B. Further Embodiments of Glenospheres for Augmented Fixation and Related Methods Referring now to FIGS. 14-22, various embodiments of glenospheres for augmented fixation are illustrated. The glenospheres described with reference to FIGS. 14-22 can be similar to the glenosphere 100 described with references to FIGS. 1-13, and can be configured to engage or otherwise interact with various baseplates, including the plate 200 described with reference to FIGS. 1-13. While the hood feature and offset engagement axis for glenospheres is described herein with reference to FIGS. 14-22, the glenosphere 100 of FIGS. 1-13 can also include a hood or other extended structure (e.g., an hood located in or around the second region 180 of the glenosphere 100). In some embodiments, a glenosphere having a hood is kinematically advantageous for a patient with a shoulder prosthesis, as the hood provides an additional point of contact between the shoulder prosthesis and a shoulder bone to prevent rocking (e.g., unintended movement of the glenosphere, such as rotation in a coronal plane of a body of a patient) as the patient moves an arm connected to the shoulder by the glenosphere. In some embodiments, a glenosphere having an engagement axis that is offset or spaced from a center of the glenosphere can improve the kinematics of the glenosphere by increasing the effective surface area of the shoulder bone that can be engaged by the glenosphere (or the glenosphere together with the baseplate) without significantly increasing the form factor of the glenosphere. In some embodiments, such as where the glenosphere includes one or more channels for receiving glenosphere fixation members that attach the glenosphere to the shoulder bone, the offset engagement axis and hood may cooperate to provide greater freedom in selecting the orientation of the channels and thus the portions of the shoulder bone at which the shoulder prosthesis is fixated.

Figure 14:
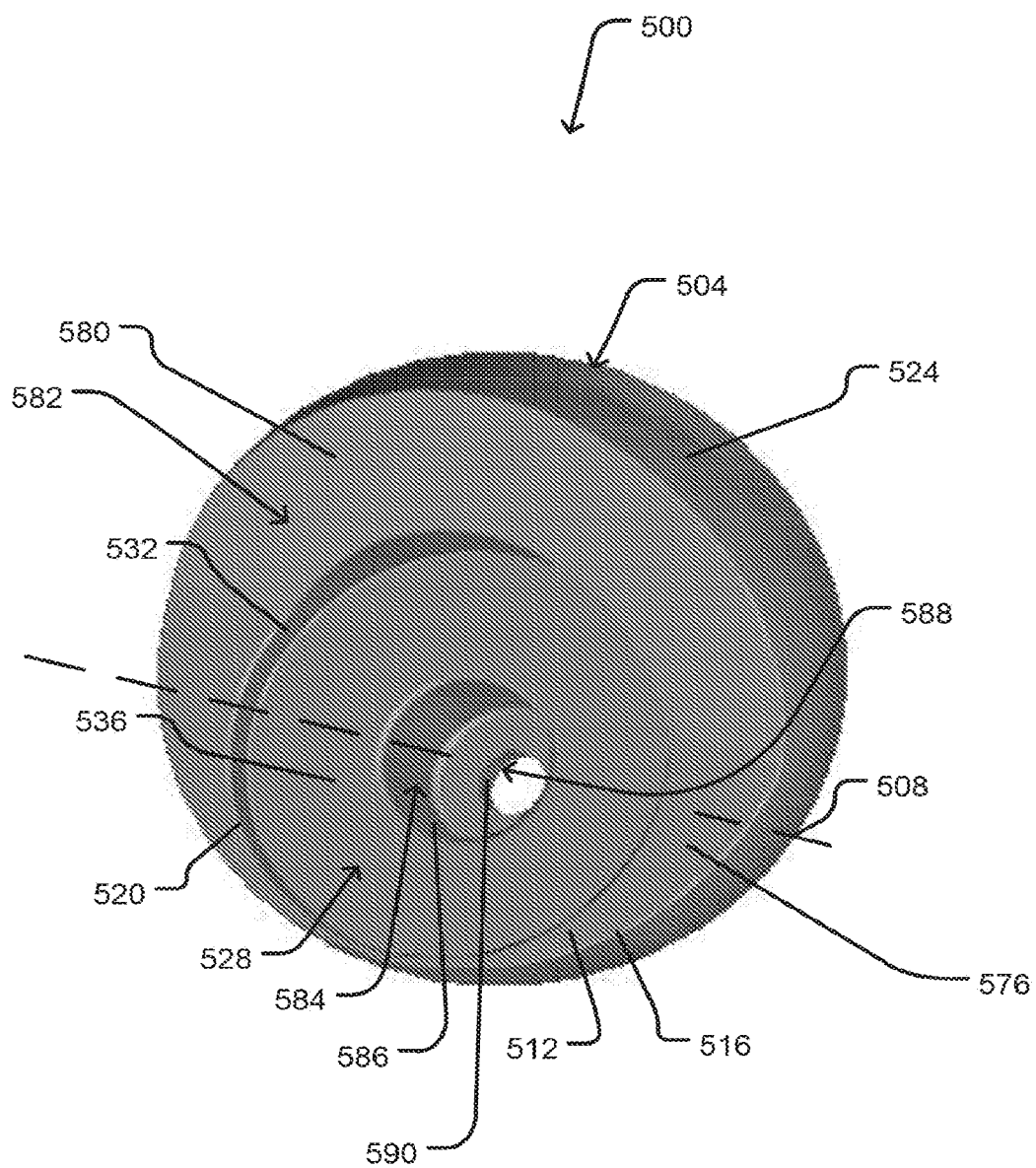
FIG. 14 is a perspective view of an embodiment of a glenosphere having a hood portion.
Figure 15:
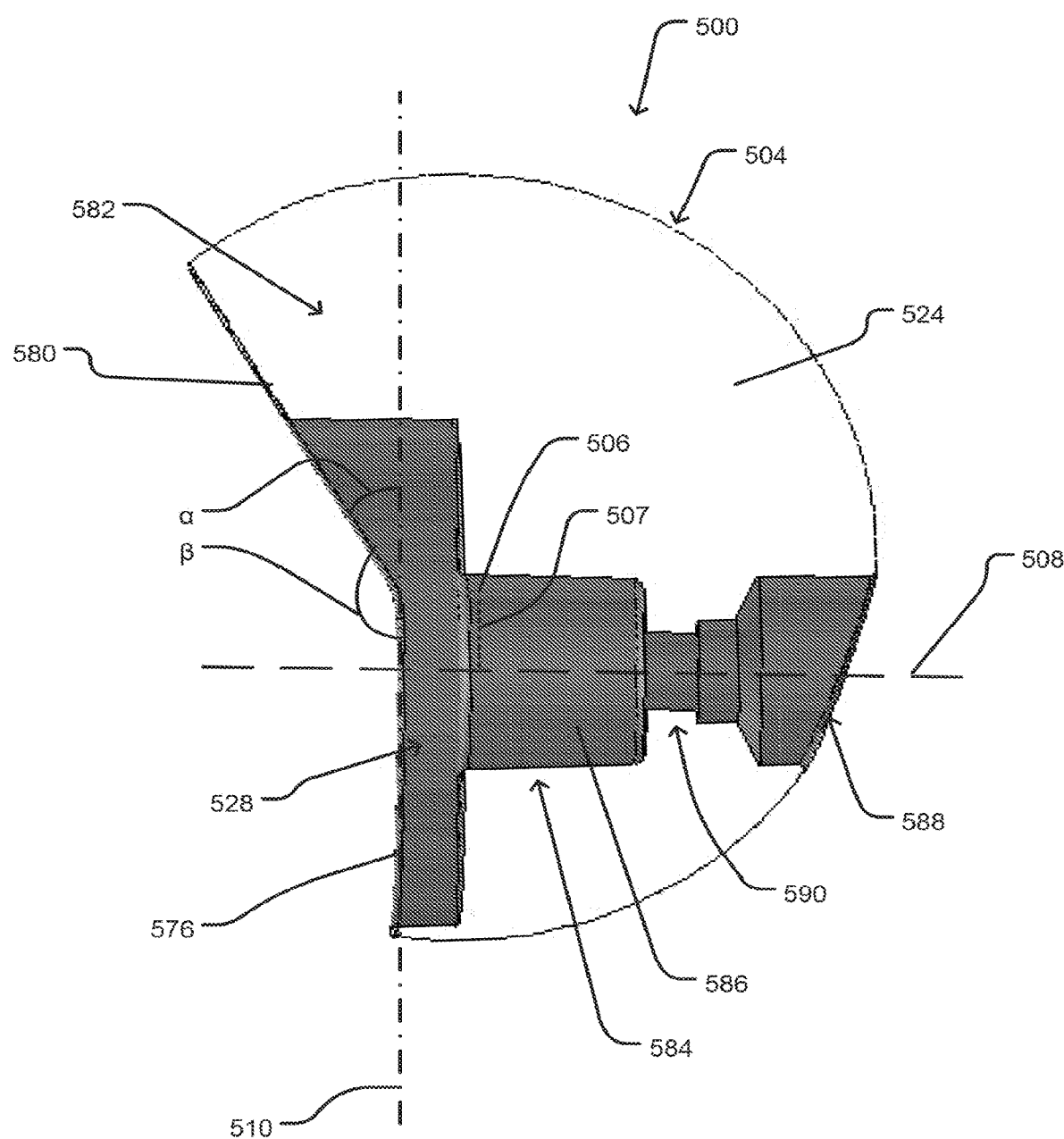
FIG. 15 is a sectional view of an embodiment of the glenosphere of FIG. 14.

Referring now to FIGS. 14-15, a glenosphere 500 is shown. The glenosphere 500 can be similar in structure and function to various glenospheres described herein (e.g., glenosphere 100). The glenosphere 500 includes a body 504 defining a center 506 and an engagement axis 508 passing through the body 504. The glenosphere 500 includes a first surface 512 including a first rim 516 and a second rim 520, the first rim 516 positioned radially outward from the second rim 520.

The glenosphere 500 also includes a second surface 524 extending from the first rim 516 of the first surface 512. The second surface 524 can have a convex shape. The second surface 524 can have a spherical shape (e.g., all or substantially all points on the second surface are equidistant from a center point, such as a center of the glenosphere 500). The second surface 524 and first surface 512 can extend from each other along an edge between the first surface 512 and the second surface 524, the edge defining a closed path about the body 504. Unlike the second surface 124 of the glenosphere 100, the second surface 524 has a continuous shape (e.g., the second surface 524 is not interrupted by openings), as the glenosphere 500 does not include a plurality of channels for receiving fixation members for attaching the glenosphere 500 to the shoulder bone; instead, by coupling to a plate (e.g., plate 200), the glenosphere 500 is attached to the shoulder bone.

The center 506 can be defined based on the second surface 524. For example, the center 506 can be a point that is equidistant from every point of the second surface 524, or a point that is equidistant from the most points on the second surface 524. In some embodiments, where a humeral component (not shown) is configured to articulate about the second surface 524, the center 506 will thus be a center for movement of the humeral component.

Similar to the central axis 108 of the glenosphere 100, the engagement axis can be an axis transverse to which a plate (e.g., plate 200) is received in the glenosphere 500 (e.g., transverse to cavity surface 532 as described below). In embodiments where the plate includes a bone engagement member (e.g., bone engagement member 204) that is centrally oriented on the plate, the bone engagement member will align with the engagement axis 508.

In some embodiments, the first surface 512 includes a base surface portion 576 and a hood surface portion 580. The hood surface portion 580 extends from the base surface portion 576. For example, as shown in FIG. 14, the hood surface portion 580 is continuous with the base surface portion 576. A plane 510 can be defined by or include the base surface portion 576. For example, as shown in FIGS. 14-15, the base surface portion 576 is substantially planar (e.g., any set of three points selected on the base surface portion 576 can define the same plane 510). As shown in FIG. 15, the hood surface portion 580 can be oriented at an acute angle α relative to the plane 510, and/or at an obtuse angle β relative to the base surface portion 576. The glenosphere 500 includes a hood portion 582 between the hood surface portion 580 and the plane 510. As shown in FIG. 15, the hood surface portion 580 is substantially planar (e.g., any set of three points selected on the hood surface portion 580 can define the same plane, that plane being oriented at the angle α relative to the plane 510). In some embodiments, the hood portion 582 is on an opposite side of the center 506 from the engagement axis 508. In some embodiments, the hood portion 582 is angled (e.g., angled relative to another portion of the body 504, such as by having the hood surface portion 580 oriented at an acute angle α relative to the plane 510, and/or at an obtuse angle β relative to the base surface portion 576).

The glenosphere 500 includes a cavity 528. The cavity 528 is configured to receive an attachment structure attachable to a bone (e.g., a plate such as plate 200). The cavity 528 is defined within the body 504. The cavity includes a perimeter defined by the second rim 520. The cavity can include a first cavity portion (e.g., a first cavity portion including a cavity wall 532 and a cavity surface 536), and a second cavity portion (e.g., inner cavity portion 584). The first cavity portion can be configured to engage with an attachment structure attachable to the shoulder bone (e.g., the plate 200). In some embodiments, rather than a cavity defined within the body 504 or recessed from the first surface 512, the glenosphere includes a plate receiver portion of the first surface 512 configured to receive and attach to the plate 200 (e.g., the plate receiver portion can be or include an engagement feature configured to couple to an engagement member of the plate 200).

The inner cavity portion can define an inner cavity surface 586. In some embodiments, the inner cavity surface 586 tapers (e.g., decreases in radius) from a first end at the cavity surface 536 to a second end at a second surface rim 588 defined on the second surface 524. In some embodiments, an inner body surface 590 is defined in the body 504 and extends between the second surface rim 588 and the inner cavity surface 586. In some embodiments, the inner cavity portion 584 is configured to or shaped and sized to engage an engagement member of the attachment structure (e.g., to engage second engagement member 236 of plate 200). As shown in FIG. 14, the inner cavity portion 584 can be oriented along the engagement axis 508 (e.g., a plane perpendicular to the inner cavity surface 586 is also perpendicular to the engagement axis 508). In some embodiments, the cavity 528 (e.g., the cavity wall 532 and/or the inner cavity surface 586) has a cylindrical or tapered cylindrical (e.g., frustrum-like) shape.

In some embodiments, the base surface portion 576 and/or the hood surface portion 580 may have non-planar shapes (e.g., curved, concave, etc.). In such embodiments, the hood portion 582 may be defined as a portion of the body 504 between the hood surface portion 580 and the plane 510, or between the hood surface portion 580 and a plane that (1) passes through (or includes) a point (or an arc segment) where the first surface 512 intersects the second surface 524, and (2) is parallel to the cavity surface 536, is perpendicular to the cavity wall 532, and/or is parallel to at least a portion of an intersection of the cavity surface 536 and the cavity wall 532. The hood portion 582 may thus extend towards a shoulder bone relative to the base surface portion 576, with an end of the hood portion 582 that is furthest from the base surface portion 576 being closest to the shoulder bone, when a plate is received in the glenosphere 500 and the glenosphere 500 and plate are attached to the shoulder bone.

In some embodiments, the base surface portion 576 and the hood surface portion 580 can form a single, substantially planar or planar surface (rather than the hood surface portion 580 being at an angle to the base surface portion 576). If the cavity 528 is recessed from the base surface portion 576, then the hood portion 582 can be defined as a portion of the body 504 between (1) a plane transverse to the cavity, such as that is tangent to the cavity wall 532 at the farthest point along the cavity wall 532 from where the cavity wall 532 is closest to the second surface 524, and (2) a plane that includes at least some points on the cavity surface 536.

The engagement axis 508 can be an axis perpendicular to a surface against which the plate is received (e.g., cavity surface 532), or an axis perpendicular to the most points on the surface (e.g., cavity surface 532). The engagement axis 508 can pass through a channel defined by the inner cavity surface 586, and/or can be defined to be equidistant from all (or the most) points on the inner cavity surface 586.

In some embodiments, such as shown in FIG. 15, the center 506 is spaced by an offset 507 from the engagement axis 508. The offset 507 increases a distance between the hood surface portion 580 and the engagement axis 508, and thus may increase a distance between the hood surface portion 580 and a plate received by the glenosphere 500 (e.g., received in cavity 528). In some embodiments, the spacing caused by the offset 507 allows the hood surface portion 580 to engage portions of a shoulder bone that would not otherwise be accessible.

In some embodiments, the hood surface portion 580 includes a rough surface, or other surface configured to engage a shoulder bone. For example, the hood surface portion 580 can have a surface with a coefficient of friction that is greater than a coefficient of friction of the base surface portion. The rough surface can facilitate frictional engagement between the hood surface portion 580 and a first portion of the shoulder bone to prevent rocking of the glenosphere 500 when the glenosphere 500 is attached to a second portion of the shoulder bone (e.g., when the glenosphere 500 is coupled to the plate 200, the plate 200 being fixated to the second portion of the shoulder bone).

Figure 16:
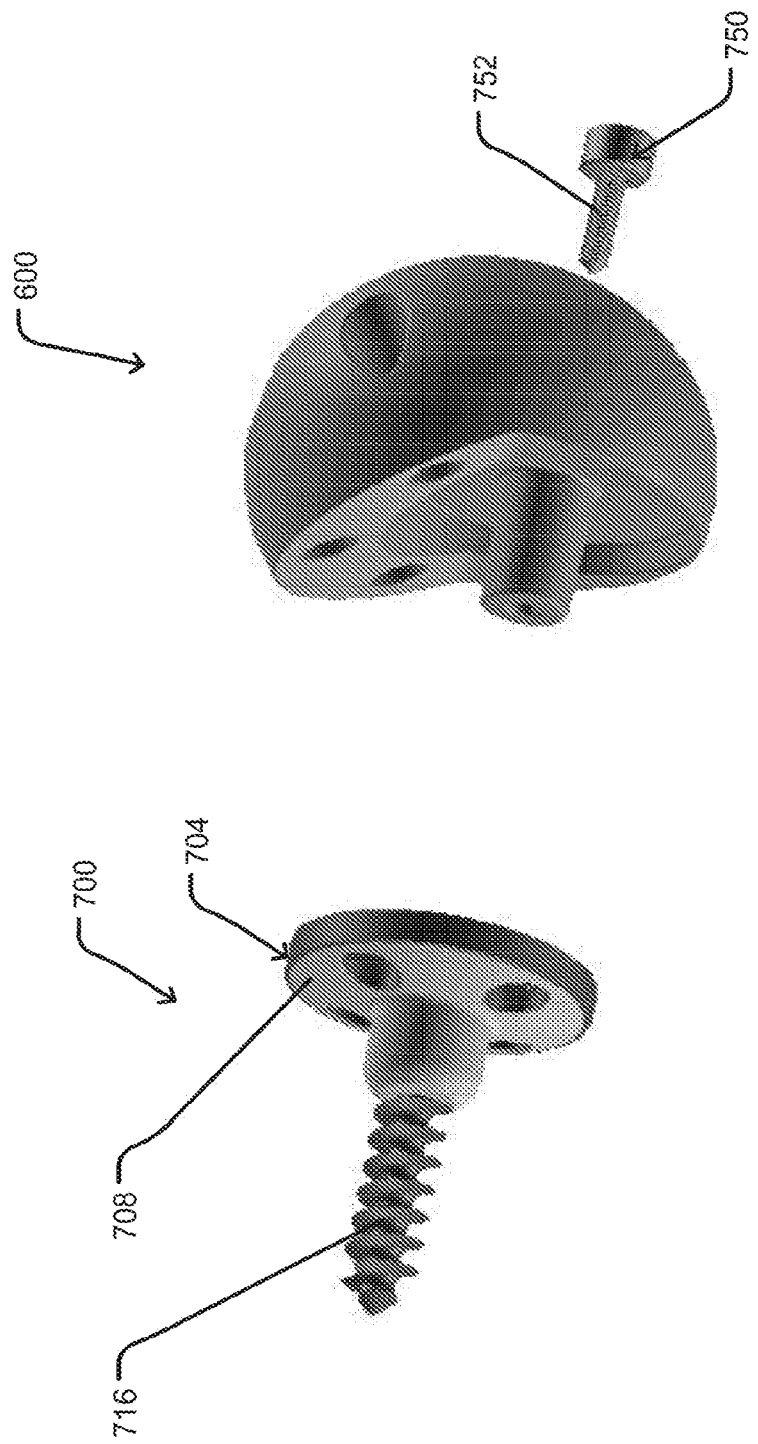
FIG. 16 is an exploded perspective view of an embodiment of a glenosphere, a plate, and a fastening member for fastening the glenosphere to the plate.
Figure 17:
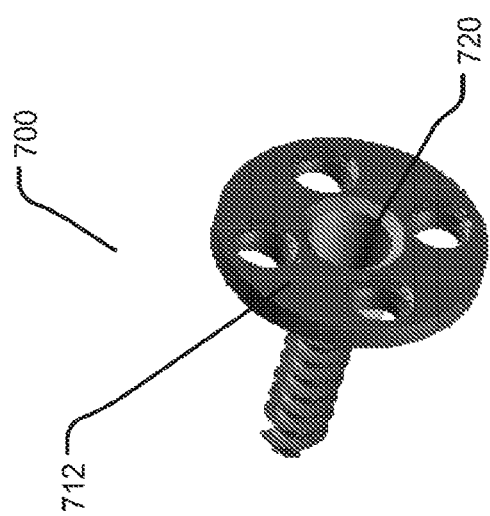
FIG. 17 is a perspective view of an embodiment of the plate of FIG. 16.
Figure 18:
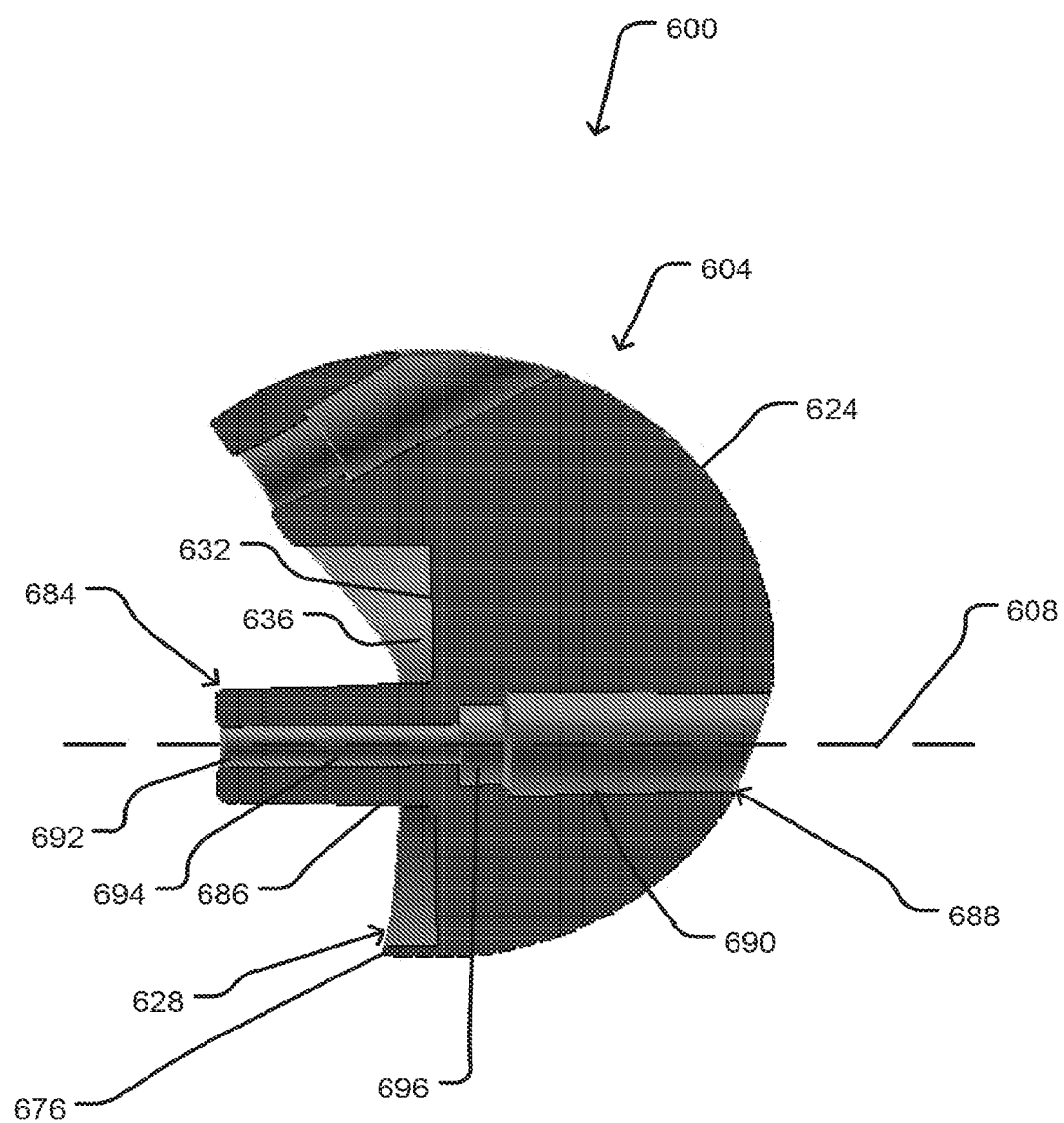
FIG. 18 is a sectional view of an embodiment of the glenosphere of FIG. 16.

Referring now to FIGS. 16-18, a glenosphere 600 is illustrated. The glenosphere 600 can be similar in structure and function to various glenospheres described herein (e.g., glenosphere 500), with the exception of the cavity of the glenosphere 600 as described further below. The glenosphere 600 can be configured to attach to a plate 700. The plate 700 can be similar in structure and function to the plate 200. The plate 700 includes a plate body 704 having a first plate surface 708 on a same side as a bone fixation member 716, and a second plate surface 712 opposite the first plate surface 708. The plate 700 also includes an engagement feature 720. As shown in FIG. 17, the engagement feature 720 includes a recess (e.g., opening, channel).

As shown in FIGS. 16-18, the glenosphere 600 includes an engagement segment 684. The engagement segment 684 is shown to have a tapered cylinder shape (e.g., frustrum-like); in various embodiments, the engagement segment 684 can have various shapes, such as an non-tapered cylinder shape (e.g., the diameter of the engagement segment 684 is constant), a polygonal solid (e.g., rectangular solid), etc. The engagement segment 684 extends along the engagement axis 608. In some embodiments, the engagement segment 684 tapers from a first engagement end at which the engagement segment 684 intersects (or extends from) the cavity surface 636, to a second engagement end at which the engagement segment 684 terminates. The engagement segment 684 can be configured to engage (e.g., form a Morse taper, attach to, receive or be received in, couple) the engagement feature 720 of the plate 700.

In some embodiments, the engagement segment 684 includes an outer engagement surface 686. The outer engagement surface 686 can taper from a first end adjacent to the cavity surface 632 to a second end at which the outer engagement surface 686 terminates. In some embodiments, the engagement segment 684 (and/or the outer engagement surface 686) extends from the cavity surface 632 out to a plane that is parallel to the cavity surface 632 and tangent to a point on the glenosphere body 604 furthest from the cavity surface 632.

The glenosphere 600 can include a second surface 624 that is convex or spherical. The second surface 624 can define a second surface rim 688. The second surface rim 688 is located at the intersection of the second surface 624 and an inner body surface 690 defined within the body 604. In some embodiments, the inner body surface 690 is oriented parallel to and/or along the engagement axis 608. For example, when the glenosphere 600 receives the plate 700 in the cavity 628, such that the bone fixation member 716 and the engagement feature 720 are each oriented along the engagement axis 608, the inner body surface 690 will also be oriented along the engagement axis 608, such as for receiving a fastening member through the inner body surface 690 to engage (e.g., attach to) the engagement feature 720 through the inner body surface 690.

The inner body surface 690 can be configured to receive a fastening member 750. The fastening member 750 can be configured to secure the glenosphere 600 to the plate 700, such as by providing additional fixation to the fixation between the engagement segment 684 and the engagement feature 720. The inner body surface 690 can have a radius (e.g., a radius defined from the engagement axis 608) that is greater than a maximum radius of the fastening member 750.

The engagement segment 684 can define an inner cavity surface 692. The inner cavity surface 692 can extend through an interior of the engagement segment 684. In some embodiments, the inner cavity surface 692 includes a first portion 694 extending from a terminal end of the inner cavity surface and a second portion 696 adjacent to the first portion 694.

In some embodiments, the second portion 696 is connected to the inner body surface 690. In some embodiments, the first portion 694 has a radius that is equal to or greater than a radius of threaded features 752 of the fastening member 750 (e.g., greater than by less than 10 percent, by less than 5 percent, by less than 2 percent), and the second portion 696 has a radius that is equal to or greater than a maximum radius of the fastening member 750 (e.g., greater than by less than 10 percent, by less than 5 percent, by less than 2 percent), such that the fastening member 750 can be inserted through the second surface rim 688 into the inner body surface 690 and received in the inner cavity surface 692, with the threaded features 752 aligning with the first portion 694.

In some embodiments, a continuous engagement opening (e.g., the opening is defined by one or more surfaces that are adjacent to at least one other of the surfaces of the opening) in which the fastening member 750 can be received and used to attach the glenosphere 600 to the plate 700 can be defined by the inner body surface 690 and the inner cavity surface 692.

Figure 19:
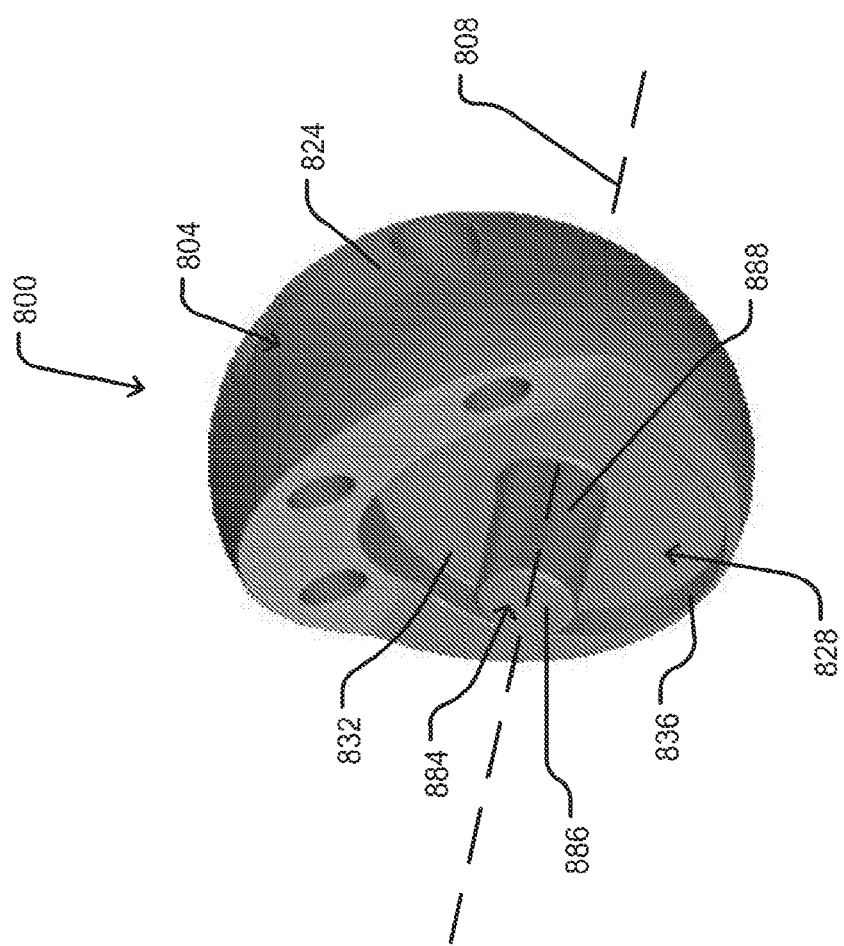
FIG. 19 is a perspective view of an embodiment of a glenosphere having an engagement segment for engaging a plate.

Referring now to FIG. 19, a glenosphere 800 is illustrated. The glenosphere 800 can be similar to various glenospheres described herein (e.g., glenosphere 800), with the exception of the engagement segment of the glenosphere 800. The glenosphere 800 includes a body 804, a second surface 824, and a cavity 828 defined at least in part by a cavity surface 832 and a cavity wall 836. An engagement segment 884 extends along an engagement axis 808 from the cavity surface 832. The engagement segment 884 can taper from a first end at which the engagement segment 884 is adjacent to the cavity surface 832 to a second end opposite the first end. Unlike the engagement segment 684 of the glenosphere 600, the engagement segment 884 does not include an inner surface in which a fastening member can be received. In other words, engagement segment 884 is defined by an outer engagement surface 888 that extends from the cavity surface 832 to a transverse engagement surface 886. The transverse engagement surface 886 defines a continuous face (e.g., the transverse engagement surface 886 is solid, does not define an opening, etc.). In addition, unlike the glenosphere 600, the second surface 924 is continuous (e.g., does not include an opening or rim such as second surface rim 688).

Figure 20:
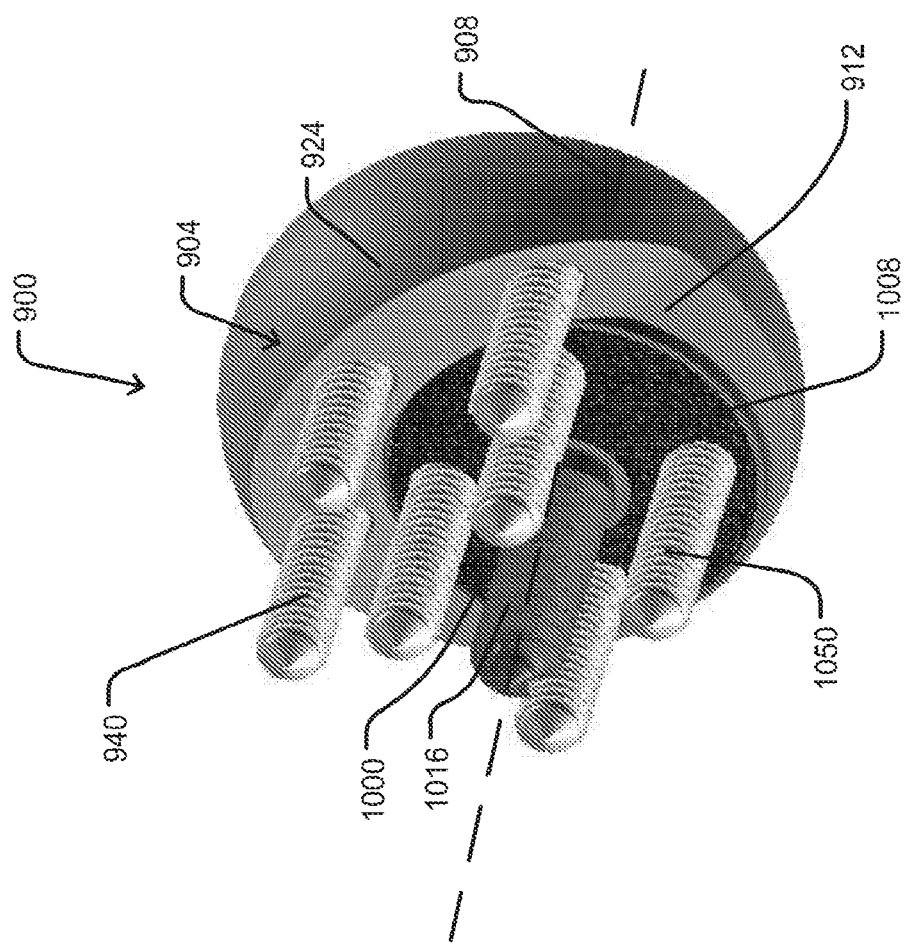
FIG. 20 is a perspective view of an embodiment of an assembly of a plate and a glenosphere in which channels of the glenosphere for receiving bone fixation members are oriented parallel to an engagement axis of the glenosphere.
Figure 21:
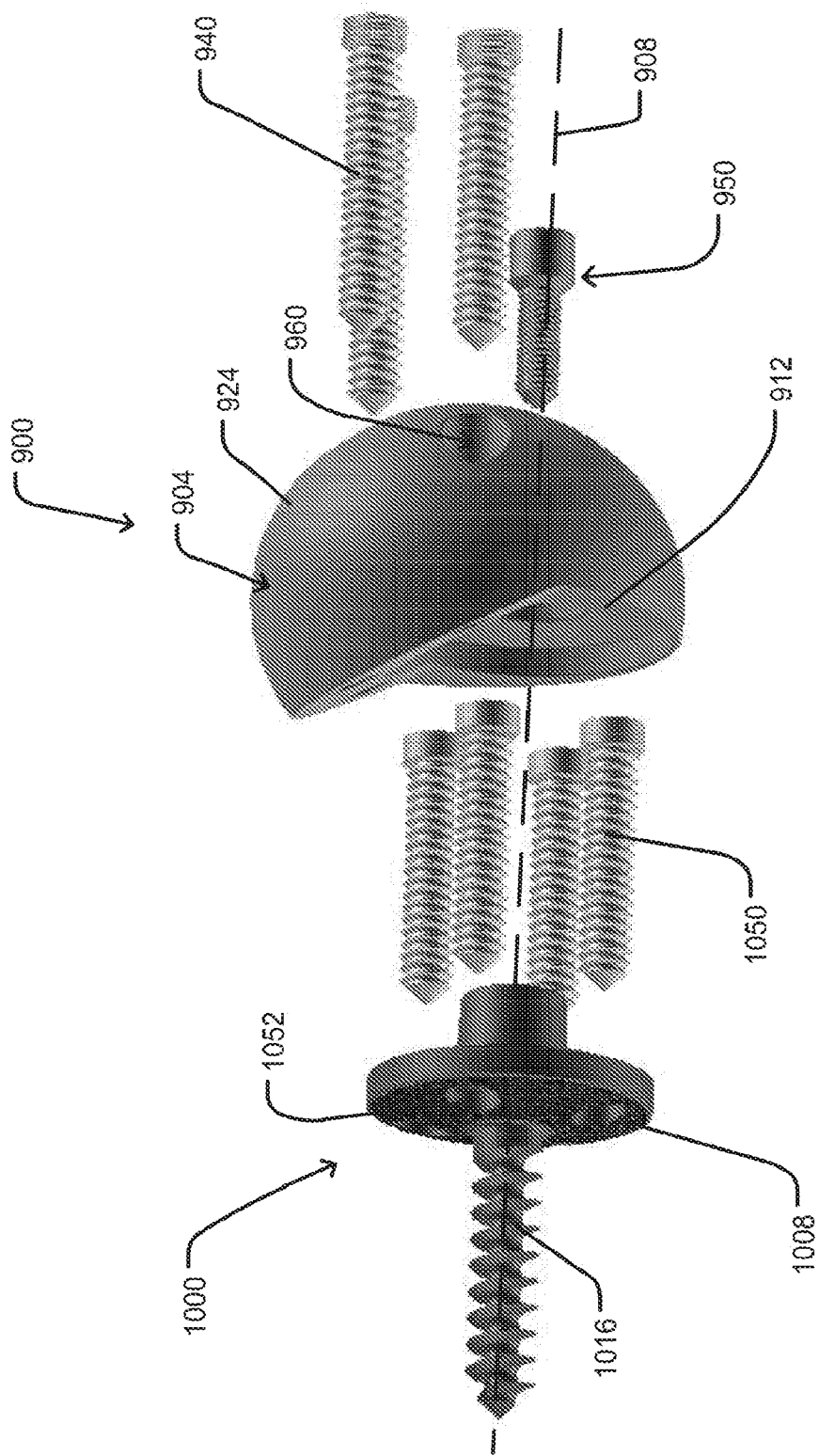
FIG. 21 is an exploded perspective view of an embodiment of the assembly of FIG. 20.
Figure 22:
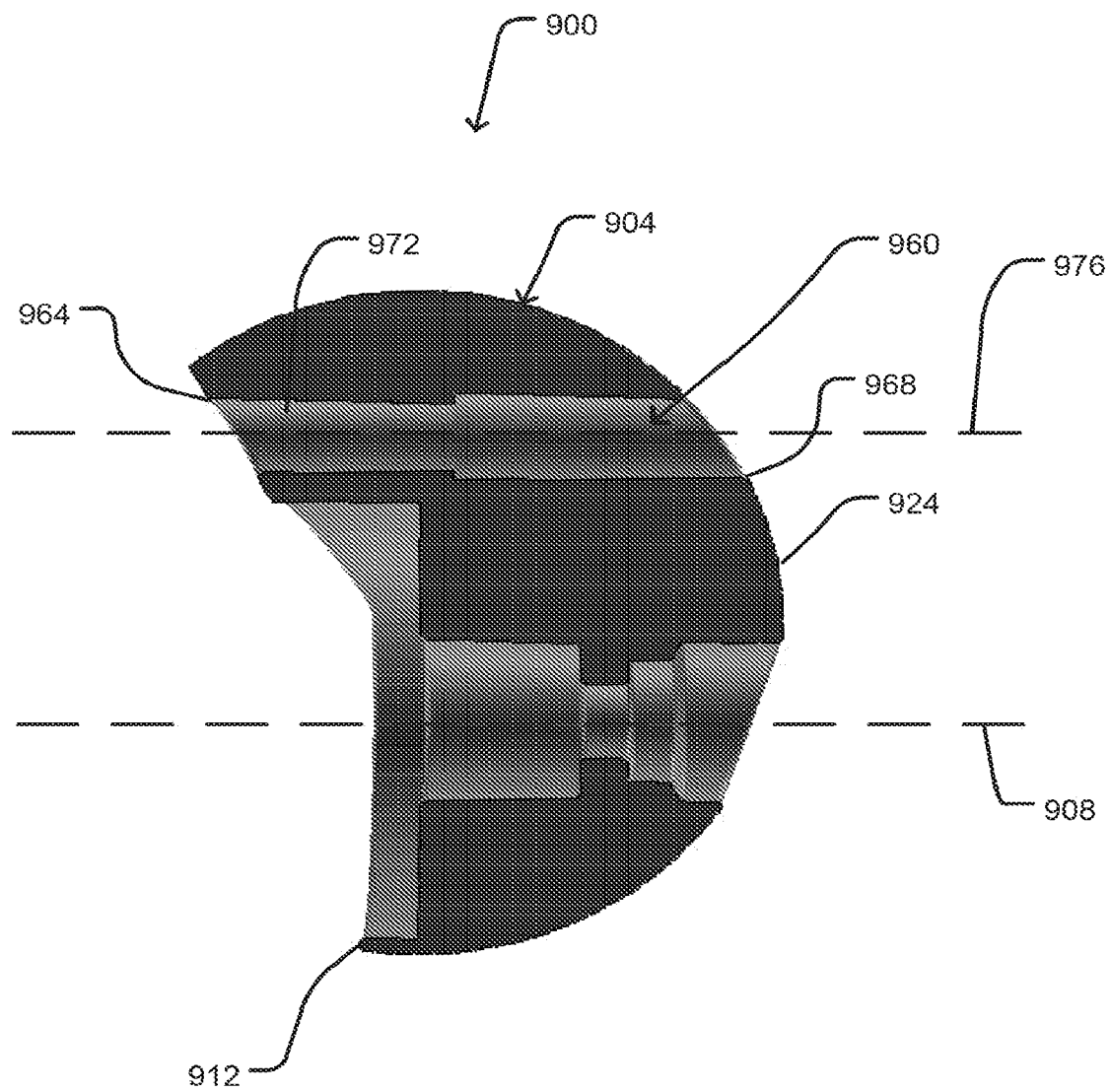
FIG. 22 is a sectional view of an embodiment of the glenosphere of FIG. 20.

Referring now to FIGS. 20-22, a glenosphere 900 is illustrated. The glenosphere 900 can be similar to various glenospheres described herein, with the exception of the orientation of channels for receiving bone fixation members. The glenosphere 900 is shown for engagement with a plate 1000. The plate 1000 can be similar to various plates described herein (e.g., plate 200, plate 700). The plate 1000 includes a plate body 1004, a first plate surface 1008, and a bone engagement member 1016 extending from a same side of the plate body 1004 as the first plate surface 1008.

In some embodiments, the first plate surface 1008 includes engagement features (e.g., relatively rough features as shown in FIGS. 20-21) that facilitate bone growth, such as for augmenting fixation between the plate 1000 and a shoulder bone. The plate 1000 can receive plate fixation members 1050 through plate channels 1052.

The glenosphere 900 includes a body 904 having a first surface 912 and a second surface 924. The glenosphere 900 defines an engagement axis 908. The glenosphere 900 includes one or more channels 960 that can receive bone fixation members 940 for attaching the glenosphere 900 to a shoulder bone. As shown in FIG. 22, the channel(s) 960 can be defined by a first channel opening 964 on the first surface 912, a second channel opening 968 on the second surface 924, and a channel surface 972 connecting the first channel opening 964 to the second channel opening 968.

Unlike the channels 160 of the glenosphere 100, the channel 960 is oriented to be parallel to the engagement axis 908, such that a bone fixation member 940 received through the channel 960 would be oriented parallel to the engagement axis 908, and/or the bone engagement member 1016 and/or plate fixation members 1050 when the glenosphere 900 is attached to the plate 1000 and the shoulder bone. For example, the channel 960 can define a channel axis 976 that is parallel to the engagement axis 908. The channel axis 976 can be defined as the axis for which the most points defined by intersections between planes perpendicular to the axis and the channel surface 972 are equidistant from the axis (e.g., the channel axis 976 is centrally oriented for the most or all cross-sections of the channel surface 972 that are perpendicular to the channel axis 976).

In some embodiments, orienting the channels 960 to be parallel to the engagement axis 908 allows the glenosphere 900 to secure a greater surface area or disparate surface areas of the shoulder bone (though the glenosphere 900 may have a less secure attachment to a specific surface area of the shoulder bone as compared to the glenosphere 100).

In some embodiments, a glenosphere includes a spherical body. The spherical body can include a first edge that defines a complete path about the body. A first surface can extend from a first side of the first edge, and a second surface can extend from a second side of the first edge opposite the first side. For example, the first surface can be adjacent to the second surface along the first edge, and together the first surface and the second surface can define a complete outer surface of the spherical body. The spherical body can define a center such that each point on the first surface is equidistant from the center (or such that the greatest possible number of points on the first surface are equidistant from the center). The first edge can define (or include) a first point and a second point. A first shortest path between the first point and the second point along the first surface (e.g., such that the only points on the first shortest path that coincide with the first edge are the first point and the second point) is greater than half of a circumference of a spherical region defined by all points equidistant from the center. In some embodiments, such a glenosphere can thus include a hooded portion (e.g., the second point is located on the hooded portion), or has a greater-than-hemispherical form factor.

C. Glenosphere with Flange for Augmented Fixation and Related Methods

Referring now to FIGS. 23-27B, various embodiments of glenospheres including a flange-type component for augmented fixation are illustrated. The glenospheres described with reference to FIGS. 23-27B can be similar to the glenospheres described with reference to FIGS. 1-22, and can be configured to engage or otherwise interact with various baseplates. In some embodiments, a glenosphere having a flange component is kinematically advantageous for a patient having a shoulder prosthesis, as the flange enables the glenosphere to contact and be supported against a greater surface area of the shoulder bone surrounding a fixation site at which fixation elements of the glenosphere and/or baseplate are secured, helping to stabilize the glenosphere against rocking or other disadvantageous movements. In some embodiments, a glenosphere having a surface for receiving the baseplate that is offset relative to the center of the glenosphere can advantageously bring the flange closer to the shoulder bone and/or away from a fixation site at which the baseplate is fixated to the shoulder bone, further improving stability. In some embodiments, the flange can facilitate distribution of forces between the shoulder prosthesis and the baseplate that could otherwise damage the baseplate. The flange can be configured to be positioned in or contact a superior aspect of the glenoid cavity. Unlike existing systems in which portions of a glenosphere may extend beyond a hemispherical shape or arrangement, but which cannot improve operation in bone loss applications, a glenosphere having a flange according to various embodiments of the present disclosure can advantageously improve operation of a shoulder prosthesis in applications with bone loss (e.g., bone loss model applications).

Figure 23A:
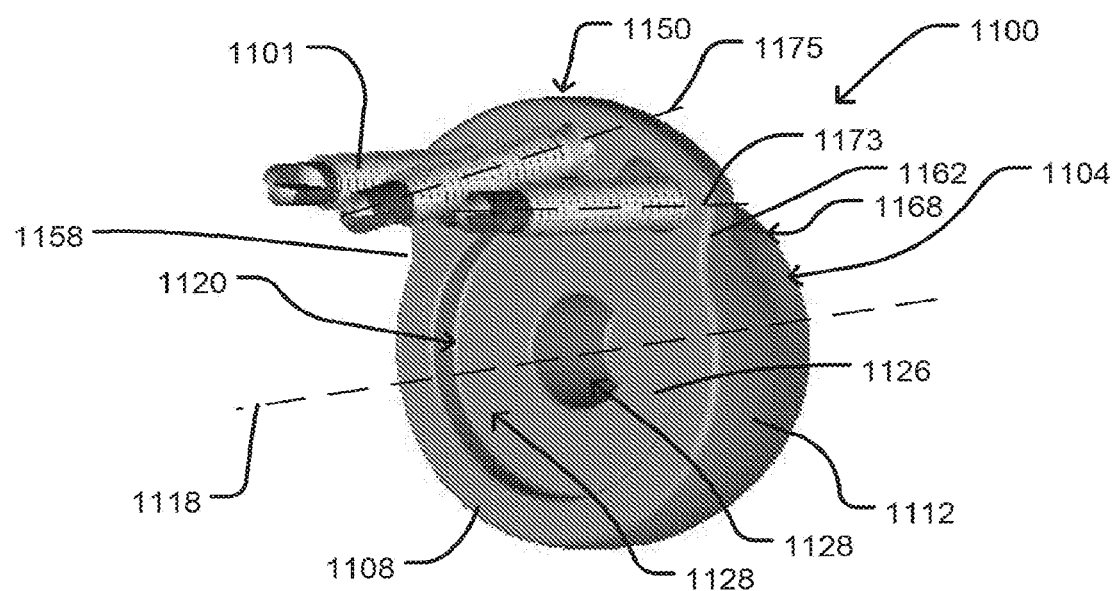
FIG. 23A is a perspective view of an embodiment of a glenosphere including a flange.
Figure 23B:
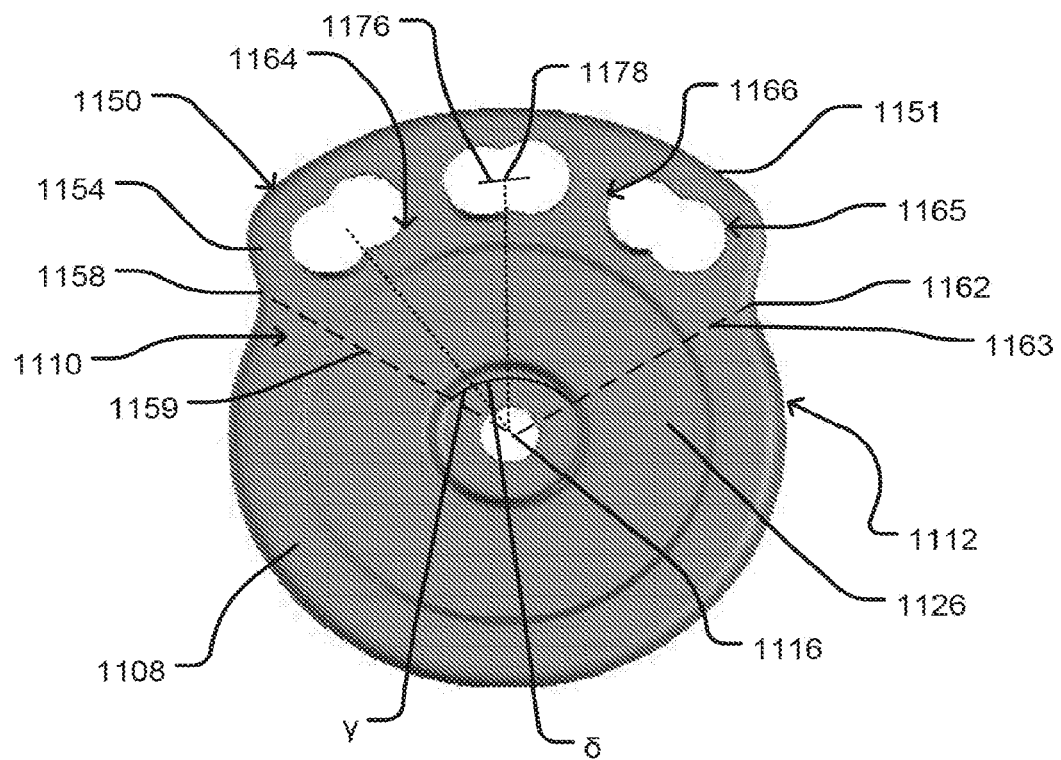
FIG. 23B is a front view of an embodiment of the glenosphere of FIG. 23A.
Figure 23C:
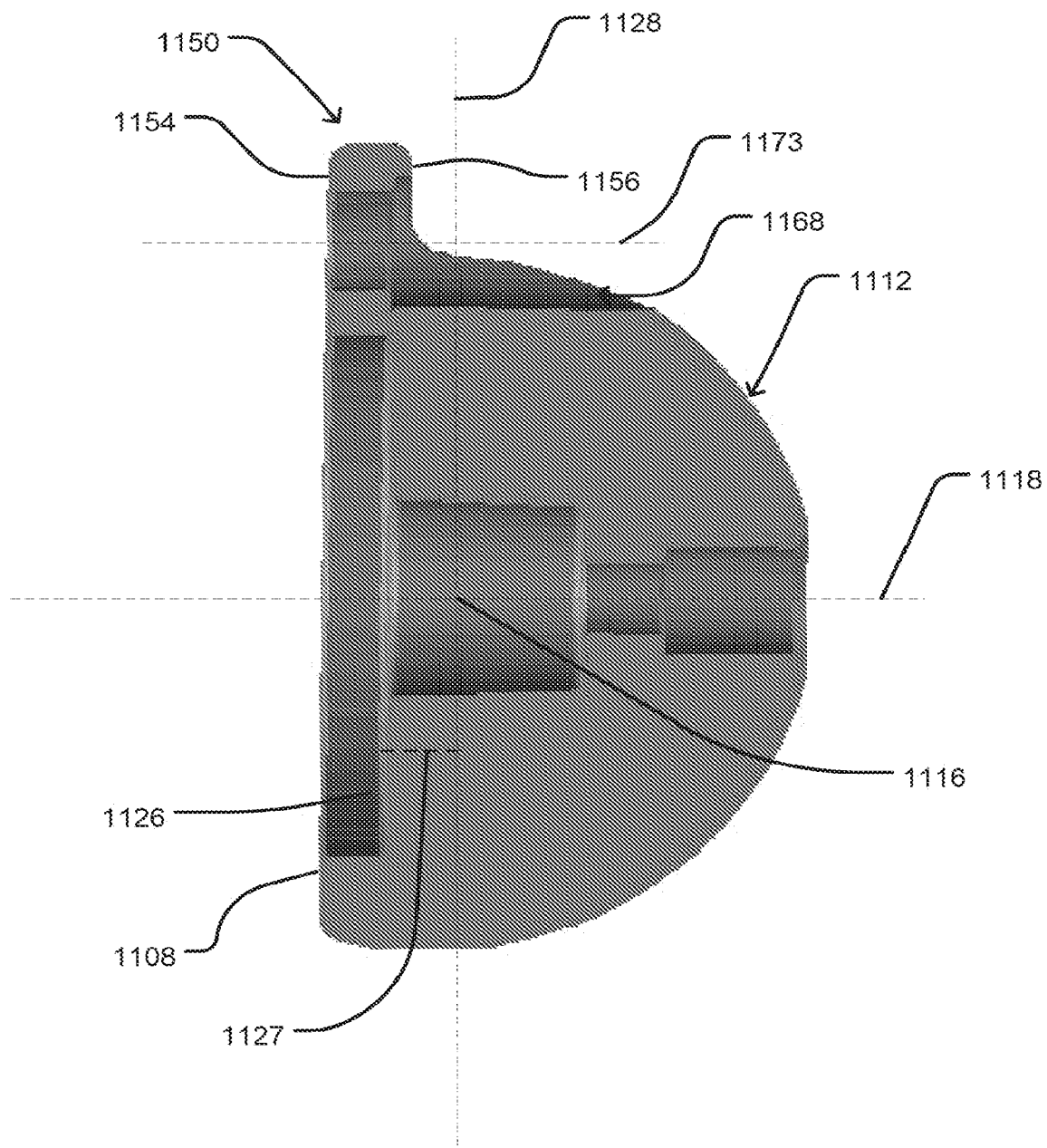
FIG. 23C is a cross-sectional view of an embodiment of the glenosphere of FIG. 23A.

Referring now to FIGS. 23A-23C, a glenosphere 1100 is shown. The glenosphere 1100 can be similar in structure and function to various glenospheres described herein. The glenosphere 1100 includes a body 1104 and a flange 1150. The body 1104 includes a first body surface 1108 and a second body surface 1112. The second body surface 1112 can be spherical (e.g., define a surface for which many, most, or all points are equidistant from a reference point, such as a center of the body 1104). The body 1104 includes an engagement feature 1120 configured to engage with an attachment structure (e.g., a plate or baseplate) attachable to the shoulder bone.

In some embodiments, the body 1104 has or defines a center 1116. The center 1116 can be a point that equidistant from many, most, or all points on an exterior of the body 1104, and/or equidistant from many, most, or all points of the second body surface 1112. In some embodiments, the center 1116 can be a center of rotation for a humeral component (not shown) coupled to the body 1104 and configured to articulate about the second body surface 1112.

The engagement feature 1120 can be a cavity similar to various embodiments of cavities as described herein. As shown in FIGS. 23A-23C, the engagement feature 1120 includes a first cavity portion 1124 configured to receive an attachment structure (e.g., a plate), and a second cavity portion 1132 configured to engage the attachment structure. The first cavity portion 1124 can include a cavity surface 1126 (e.g., an engagement surface) against which the attachment structure can be positioned or received. In some implementations, the cavity surface 1126 may be separated from the first body surface 1108 by a wall defining a depth of the cavity.

The body 1104 can define an engagement axis 1118. The engagement axis 1118 can be an axis passing through the engagement feature 1120 and indicating a direction against which the glenosphere 1100 generally is brought towards the shoulder bone. In some embodiments, the engagement axis 1118 is perpendicular or substantially perpendicular to the cavity surface 1126. The engagement axis 1118 may align with a plate fixation member of the plate when the plate is received in the first cavity portion 1124. In some embodiments, such as shown in FIG. 23C, the engagement axis 1118 passes through (e.g., includes, is collinear with) the center 1116.

In some embodiments, the engagement feature 1120 and/or the cavity surface 1126 is offset by an engagement offset 1127 from the center 1116 of the body 1104 (or from a plane 1128 including the center 1116 and parallel to the cavity surface 1126 or to an outer edge of the cavity surface 1126). This offset can increase the range of motion for articulation enabled by the second body surface 1112, as the second body surface 1112 may occupy a space greater than a hemispherical space defined as being equidistant from the center 1116, and can bring the flange 1150 closer to the shoulder bone when the plate is received and secured by the engagement feature 1120 and the glenosphere 1100 is fixated to the shoulder bone. In some embodiments, the engagement offset 1127 is approximately 6 mm (e.g., greater than or equal to 4 mm and less than or equal to 8 mm; greater than or equal to 5 mm and less than or equal to 9 mm). In some embodiments, the engagement offset 1127 is approximately 10 mm (e.g., greater than or equal to 8 mm and less than or equal to 12 mm; greater than or equal to 9 mm and less than or equal to 11 mm).

The flange 1150 extends radially outward from the body 1104 and includes a first flange surface 1154 contiguous with the first body surface 1108 and a second flange surface 1156 contiguous with the second body surface 1112. The flange 1150 can extend further radially outward from the body 1104 than the second body surface 1112 (e.g., at least a portion of the flange 1150 is at a greater distance from the center 1116 than any point on the second body surface 1112). In some embodiments, the flange 1150 has a flange length (e.g., a length defined along an outer rim 1151 of the flange 1150) extending from a first end 1158 and a second end 1162 such that an angle $\gamma$ defined by a first line 1159 from the center 1116 to the first end 1158 and a second line 1163 from the center 1116 to the second end 1162 is less than 180 degrees (e.g., less than 150 degrees, less than 120 degrees, less than 90 degrees, less than 180 degrees and greater than 45 degrees). The body 1104 can include a glenosphere body surface 1110 that includes the first body surface 1108 and the first flange surface 1154. The flange 1150 can provide additional support for the glenosphere 1100 by adding surface area for stabilizing the glenosphere 1100 against the shoulder bone. The angle $\gamma$, or other measures of a size of the flange 1150 can be selected to reduce or minimize a total size or volume occupied by the glenosphere 1100. For example, in some configurations, as the size of the flange 1150 increases, it may become more difficult to place the glenosphere 1100 in the glenohumeral joint; if a too large flange 1150 is used, it may interference with range of motion of the humerus as well as interfere with soft tissue such as the subscapularis, supraspinatus, and/or infraspinatus tissue. At the same time, increasing or maximizing a surface area of the flange 1150 that can contact the shoulder bone can increase stability of the glenosphere 1100 or otherwise improve the kinematics of the glenosphere 1100.

Figure 24:
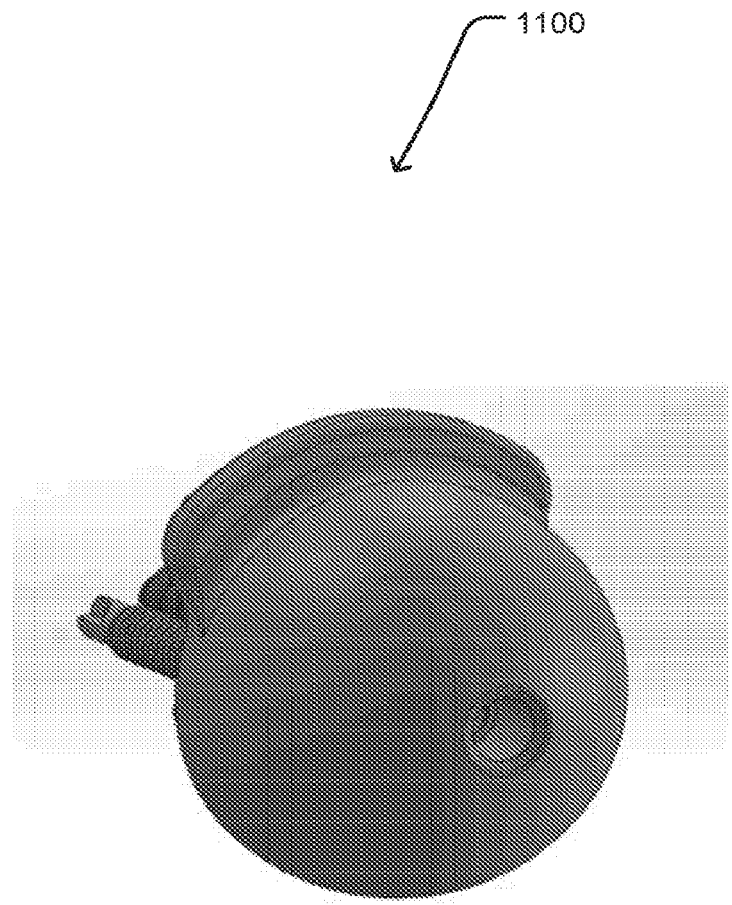
FIG. 24 is a rear perspective of an embodiment of a glenosphere including a flange.

In some embodiments, the flange 1150 includes a hole 1164 extending from a first hole opening 1166 defined by the first flange surface 1154 to a second hole opening 1168 defined by the second flange surface 1156. The hole 1164 can be configured to receive a glenosphere fixation member 1101 (e.g., a fixation member similar or identical to glenosphere fixation member 140) configured to attach the glenosphere to the shoulder bone. As shown in FIGS. 23A-23C, the glenosphere 1100 includes three holes 1164. In various embodiments, various numbers of holes 1164 can be included by the flange 1150 (e.g., 1, 2, 3, 4, 5, holes). In other embodiments (e.g., as shown in FIG. 24, the flange 1150 does not include a hole, e.g. has a continuous or uninterrupted surface).

In some embodiments, the second body surface 1112 defines a hole path 1168. The hole path 1168 can be recessed within the second body surface 1112. The hole path can be recessed towards the center 1116 (e.g., is recessed into the body 1104 from the second body surface 1112; a surface of the hole path 1168 is closer to the center 1116 than an adjacent portion of the second body surface 1112). The hole path 1168 is in communication with the second hole opening 1168 (e.g., is contiguous with, transitions to), and can guide the glenosphere fixation member 1101 into the hole 1164. When the glenosphere fixation member 1101 is received in the hole path 1168 and through the hole 1164, a portion of the glenosphere fixation member will be positioned closer to the center 1116 relative to the second body surface 1112.

The hole 1164 can be configured to receive a plurality of glenosphere fixation members 1101, or, as shown in FIGS. 23A-23C, can receive glenosphere fixation members 1101 at different positions and/or orientations. For example, the hole 1164 can be configured to receive the glenosphere fixation member 1101 at a first angle corresponding to a first channel 1165 of the hole or at a second angle corresponding to a second channel 1166 of the hole. The first channel 1165 can define a first channel axis 1173, and the second channel 1166 can define a second channel axis 1175 (e.g., the channel axes can be defined as being equidistant from many, most, or all points on the corresponding surfaces). The channels 1165, 1166 can be contiguous with each other. The hole path 1168 can include portions aligned with each channel axis 1173, 1175.

The channels 1165, 1166 can be configured to receive and/or secure the glenosphere fixation member. For example, the channels 1165, 1166 can include thread receiving surfaces configured to engage threads of the glenosphere fixation member 1101. The first channel axis 1173 can define a channel offset 1176 from the second channel axis 1175, such that a position of the glenosphere fixation member 1101 when received in the first channel 1165 is offset from when received in the second channel 1166. In some embodiments, the channel offset 1176 is approximately 3 mm (e.g., greater than or equal to 1 mm and less than or equal to 10 mm, greater than or equal to 1 mm and less than or equal to 5 mm, greater than or equal to 2 mm and less than or equal to 4 mm, 3 mm). In some embodiments, the first channel axis 1173 is parallel to the cavity surface 1126 or the engagement axis 1118, and the second channel axis 1175 is angled towards the cavity surface 1126 or the engagement axis 1118 relative to the first channel axis 1173 (e.g., angled by 10 degrees, by an angle greater than or equal to 5 degrees and less than or equal to 20 degrees; greater than or equal to 7.5 degrees and less than or equal to 15 degrees; greater than or equal to 9 degrees and less than or equal to 11 degrees). The angle between the first channel axis 1173 and the second channel axis 1175 can provide more options for orienting and implanting the glenosphere 1100 in patients having varied sizes and/or glenoid bone loss in the glenoid cavity. As the angle increases, there may be more options for where the glenosphere fixation member can be fixed to the shoulder bone. For example, the angle can enable the glenosphere fixation member to be fixed to a bone location (e.g., a bone location that increases or optimizes stability) at the base of the coracoid or the acromion.

The hole 1164 can define a hole center 1178 that is equidistant from the channel axes 1173, 1175, and falls within (e.g., is included within) a plane that includes the channels 1165, 1166. In embodiments where the flange 1150 includes more than one hole 1164, the channel centers 1178 can be oriented at an angle $\delta$ defined from the center 1116 (e.g., an angle defined by lines from the center 1116 to the channel centers 1178 or the channel axes 1173, 1175). The angle $\delta$ can indicate or be a measure of an arcuate range of space (or a portion thereof) covered by the flange 1150. The angle $\delta$ can be approximately 35 degrees (e.g., greater than or equal to 20 degrees and less than or equal to 50 degrees; greater than or equal to 30 degrees and less than or equal to 40 degrees; greater than or equal to 34 degrees and less than or equal to 36 degrees).

Figure 25A:
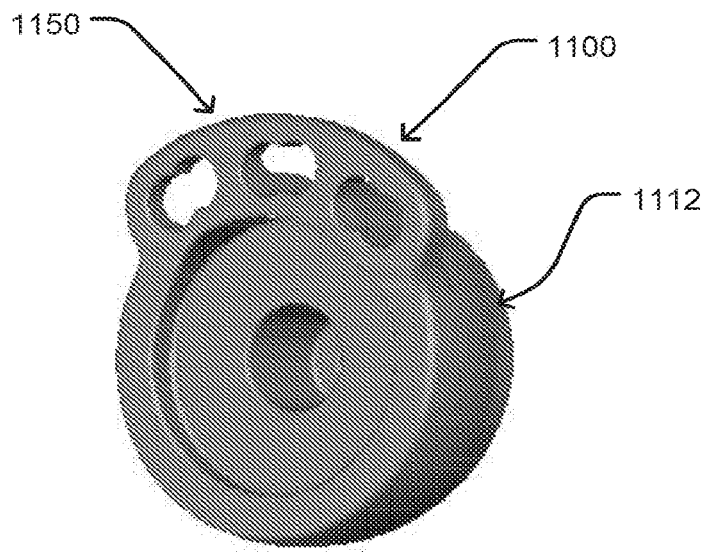
FIG. 25A is a perspective view of an embodiment of a glenosphere in which the flange is offset from a center of the glenosphere.
Figure 25B:
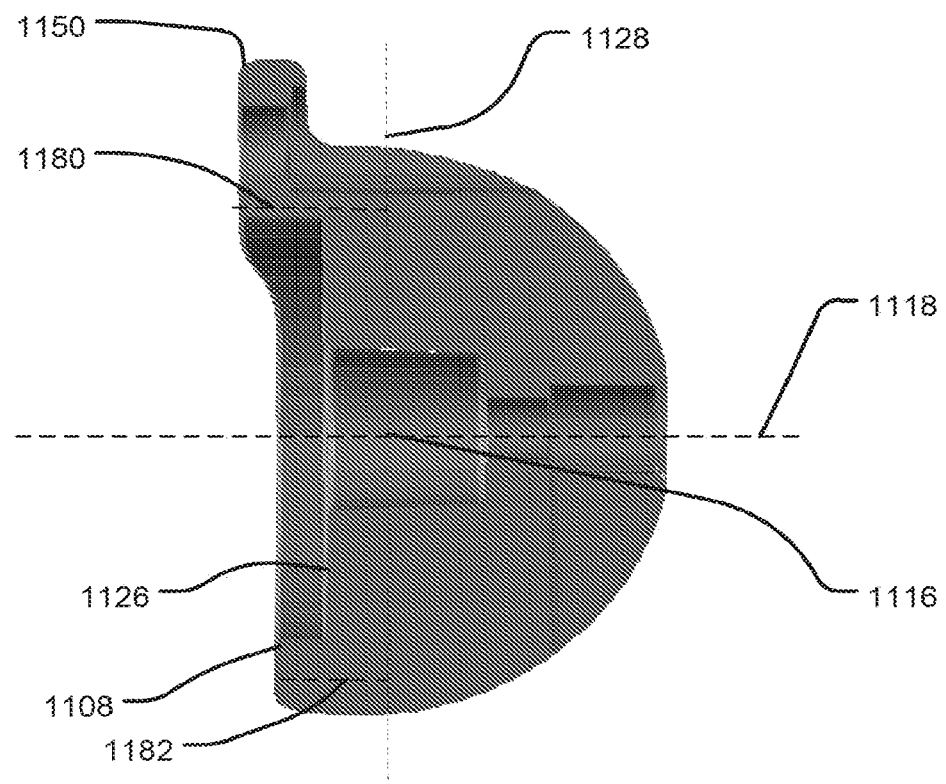
FIG. 25B is a cross-sectional view of an embodiment of the glenosphere of FIG. 25A.

Referring now to FIGS. 25A-25B, the glenosphere 1100 is shown having an offset flange 1150. In some embodiments, the flange 1150 is configured to be offset from the first body surface 1108. The flange 1150 can be offset such that the flange 1150 is closer to the shoulder bone than the first body surface 1108 when the glenosphere 1100 is secured to the shoulder bone, and/or extends out and over the plate when the plate is received and engagement by the engagement feature 1120. In embodiments where the flange 1150 is offset, the glenosphere 1100 can thus be adapted to various geometries of the shoulder bone, such as for drawing the flange 1150 closer to a portion of the shoulder bone that is away from where the plate is fixated to the shoulder bone. In some embodiments, the offset of the flange 1150 can beneficially position the channels 1165, 1166 further away from the center 1116 of the glenosphere 1100 (as compared to a glenosphere that does include the flange 1150), and thus a range of motion of a humeral component articulating about the second body surface 1112. Such positioning can reduce the likelihood of osteolysis that might result from friction between the humeral component and the glenosphere 1100 that would generate wear particles that can be pushed through the channels 1165, 1166 into the shoulder joint by the articulating humeral component.

The flange 1150 can be offset from the plane 1128 by a first offset distance 1180 (e.g., as measured to the first flange surface 1154), the first offset distance 1180 being greater than a second offset distance 1182 by which the first body surface 1108 is offset from the plane. In some embodiments, a difference between the first offset distance 1180 and the second offset distance 1182 is approximately 3 mm (e.g., greater than or equal to 2 mm and less than or equal to 4 mm), 5 mm (e.g., greater than or equal to 4 mm and less than or equal to 6 mm), or 7 mm (e.g., greater than or equal to 6 mm and less than or equal to 8 mm). The offsets may also be defined relative to a cavity surface 1126, or a plane passing through an outer edge of the cavity surface 1126.

Figure 26A:
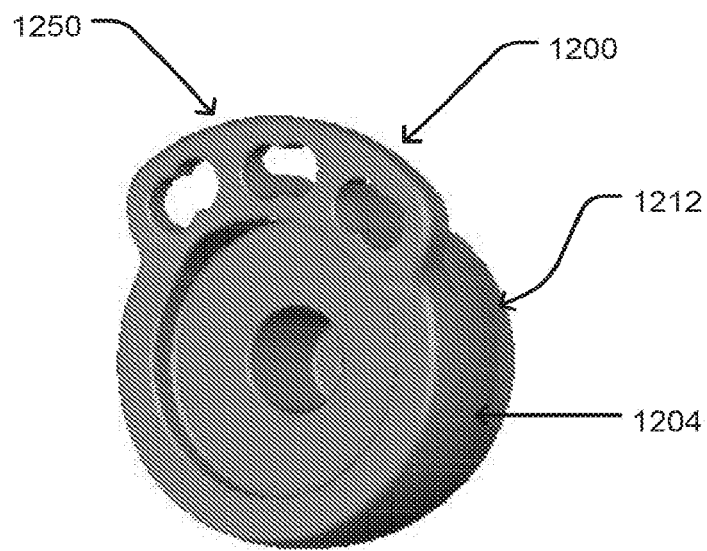
FIG. 26A is a perspective view of an embodiment of a glenosphere including an angled flange.
Figure 26B:
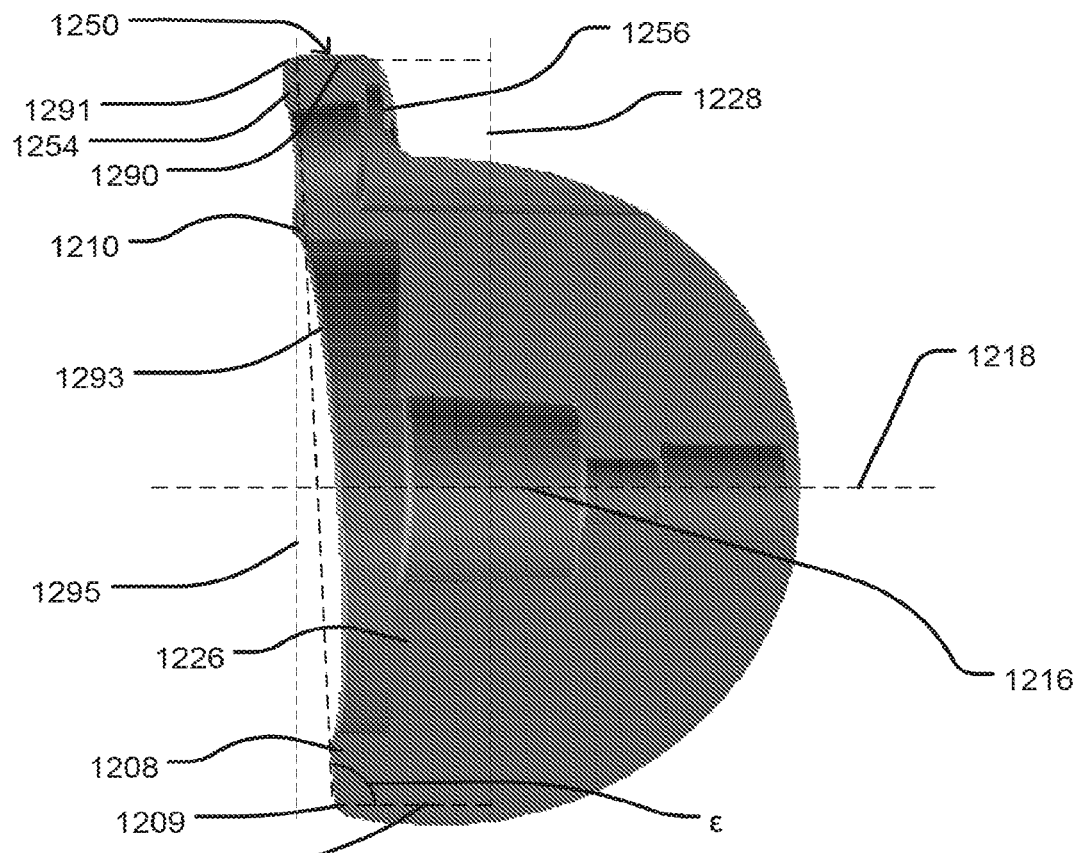
FIG. 26B is a cross-sectional view of an embodiment of the glenosphere of FIG. 26A.

Referring now to FIGS. 26A-26B, a glenosphere 1200 is shown. The glenosphere 1200 can be similar to the glenosphere 1100, with the exception of the shape and/or orientation of the glenosphere body surface (e.g., the first flange surface and/or first body surface). The glenosphere 1200 can include a body 1204, a first body surface 1208, and a second body surface 1212. The glenosphere 1200 can define a center 1216 and an engagement axis 1218. The glenosphere 1200 can include a flange 1250 extending radially outward from the body 1204. The flange 1250 can include a first flange surface 1254 and a second flange surface 1256. The glenosphere 1200 can include a glenosphere body surface 1210 including the first body surface 1208 and the first flange surface 1254. The glenosphere 1200 can define a plane 1228 that includes or passes through the center 1216.

In some embodiments, the first flange surface 1254 and/or the glenosphere body surface 1204 is oriented at an angle to the plane 1228. For example, a first end 1291 of the first flange surface 1254 (e.g., an end of the first flange surface 1254 that is further from the center 1216, the engagement axis 1218, and/or adjacent to an exterior rim of the flange 1250) can be offset by a flange offset 1290 from the plane 1228, while a second end 1209 of the first body surface 1208 (e.g., an end or point where the first body surface 1208 meets the second body surface 1212 and furthest from the flange 1250, the engagement axis 1218, and/or the center 1216) is offset by a body offset 1292 from the plane 1228, the body offset 1292 being less than the flange offset 1290. The glenosphere body surface 1210 can be planar or substantially planar. A line 1293 between the first end 1291 and the second end 1292 can define an angle c relative to the body offset 1292, or may similarly define an angle at an intersection (not shown) of the line 1293 and the plane 1228, such that the glenosphere body surface 1204 is angled relative to the plane 1228. The glenosphere body surface 1204 can be angled such that the body offset 1292 is approximately 3 mm (e.g., greater than or equal to 2 mm and less than or equal to 4 mm), 5 mm (e.g., greater than or equal to 4 mm and less than or equal to 6 mm), or 7 mm (e.g., greater than or equal to 6 mm and less than or equal to 8 mm). The body offset can also be measured from the center 1216 to a plane 1295 including or passing through the first point 1219 and parallel to the plane 1228.

Figure 27A:
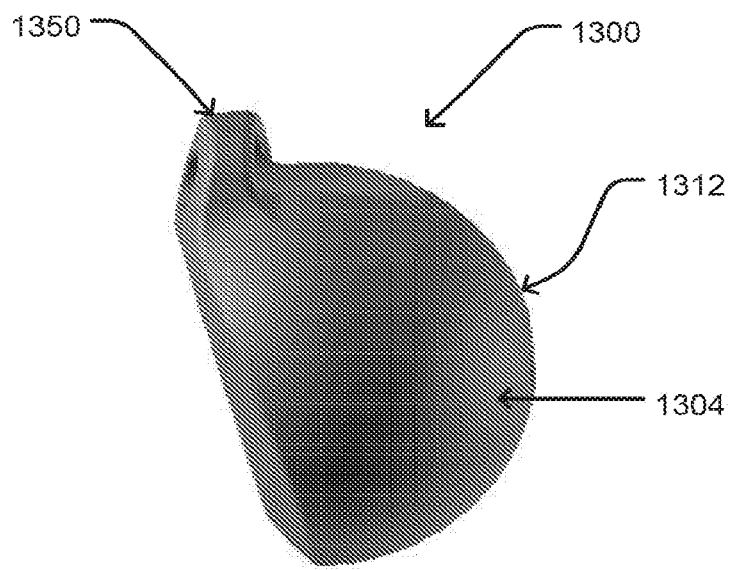
FIG. 27A is a side view of an embodiment of a glenosphere including a curved flange.
Figure 27B:
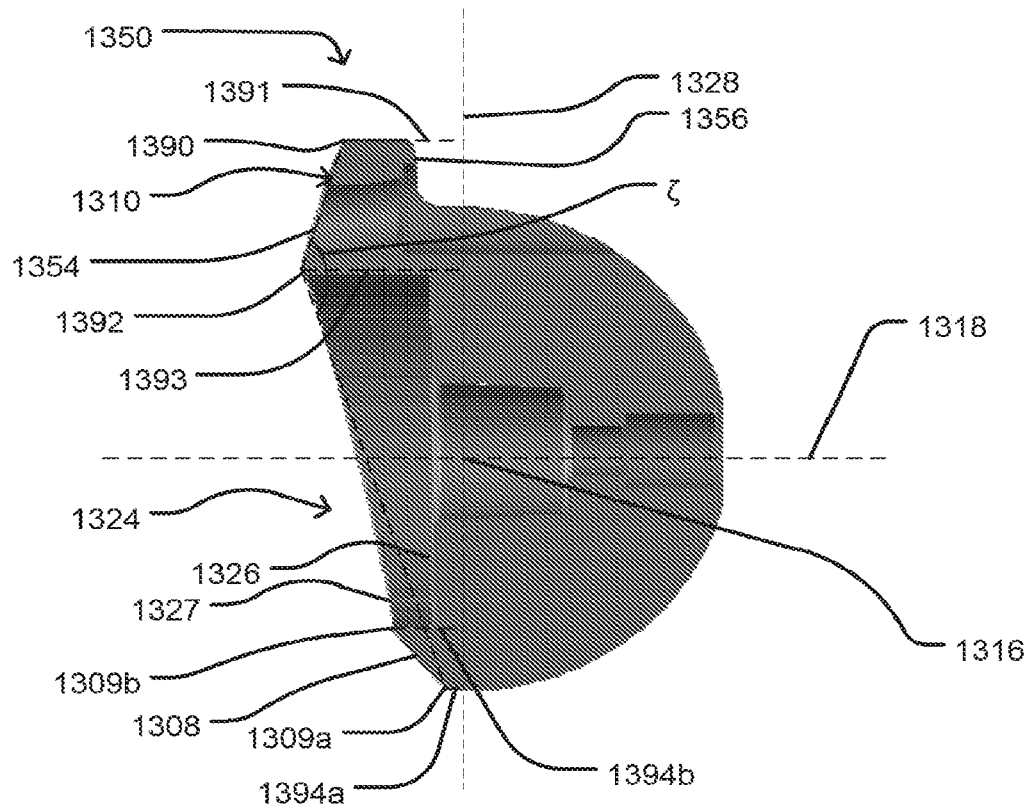
FIG. 27B is a cross-sectional view of an embodiment of the glenosphere of FIG. 27A.

Referring now to FIGS. 27A-27B, a glenosphere 1300 is shown. The glenosphere 1300 can be similar to the glenosphere 1200, with the exception of the shape of the first flange surface and/or glenosphere body surface as described herein. The glenosphere 1300 can include a body 1304, a first body surface 1308, and a second body surface 1312. The glenosphere 1300 can define a center 1316, an engagement axis 1318 passing through the center 1316, and a plane 1328 including the center 1316. A flange 1350 can extend radially outward from the body 1304 and include a first flange surface 1354 and a second flange surface 1356. A glenosphere body surface 1310 can include the first body surface 1308 and the first flange surface 1354. The glenosphere can include an engagement feature including a cavity surface 1326.

In some embodiments, the glenosphere 1300 has a curved or non-linear (or non-planar) glenosphere body surface 1310 and/or a curved or non-linear (or non-planar) first flange surface 1310. A first flange offset 1393, defined from the plane 1328 to a first flange end 1392 (e.g., a point at which the first body surface 1308 is adjacent to the first flange surface 1354), can be greater than a second flange offset 1391, defined from the plane 1328 to an outer flange end 1390 (e.g., an outermost point on the first flange surface 1354). The first flange offset 1393 can also be greater than a first body offset 1394a defined between the plane 1328 and a first body end 1309a (e.g., an outermost point of the body 1304 where the first body surface 1308 meets the second body surface 1312 and which may be furthest from the flange 1354), and may be greater than a second body offset 13094 defined between the plane 1328 and a second body end 1309b (e.g., a point at which a rim 1327 of an engagement feature 1324 intersects the first body surface 1308 and furthest from the flange 1350). The offsets may also be defined relative to a cavity surface 1326, or a plane passing through an outer edge of the cavity surface 1326. In some embodiments, the first flange end 1392 is positioned closest to the shoulder bone when the glenosphere 1300 is fixated to the shoulder bone and/or to a plate, allowing glenosphere fixation members received through the glenosphere to be closely secured to the shoulder bone while a significant portion of the body 1304 is positioned away from the shoulder bone.

In some embodiments, a glenosphere includes a body and a flange. The body includes a first body surface and a spherical second body surface and includes an engagement feature to engage with an attachment structure attachable to a bone. The flange is integral with the body, extends radially outward from the body and includes a first flange surface contiguous with the first body surface and a second flange surface contiguous with the second body surface. The flange has a flange length extending from a first end and a second end such that an angle defined by a first line from a center of the body to the first end and a second line from the center of the body to the second end is less than 180 degrees.

What is claimed is:

1. A glenosphere comprising:
a body having a bone facing surface and an opposing articulating surface; and
a flange integral with and extending from the body.

2. The glenosphere of claim 1, wherein the flange extends about a portion of a perimeter of the body.

3. The glenosphere of claim 1, wherein the flange has a bone facing surface and an opposing surface.

4. The glenosphere of claim 3, wherein the bone facing surface of the flange is non-planar.

5. The glenosphere of claim 3, wherein the bone facing surface of the flange is contiguous with the bone facing surface of the body and wherein opposing surface of the flange is contiguous with the opposing articulating surface of the body.

6. The glenosphere of claim 3, wherein bone facing surface of the flange is in a first plane and the bone facing surface of the body is in a second plane that is at a non-zero angle relative to the first plane.

7. The glenosphere of claim 1, wherein the opposing articulating surface is generally spherical.

8. The glenosphere of claim 1, further comprising an engagement feature configured to engage with an attachment structure that is attachable to a bone of a patient.

9. The glenosphere of claim 8, wherein the engagement feature includes a projection that extends from the bone facing surface of the body.

10. The glenosphere of claim 8, wherein the engagement feature includes a cavity.

11. The glenosphere of claim 1, wherein the flange includes an aperture that is configured to receive a fixation member therethrough to aid in attaching the glenosphere to bone.

12. The glenosphere of claim 11, wherein a first portion of the aperture defines a first channel and a second portion of the aperture defines a second channel.

13. The glenosphere of claim 12, wherein the first channel is oriented such that positioning of the fixation member through the first channel causes a central axis of the fixation member to have a first orientation relative to a central axis of the body and wherein the second channel is oriented such that positioning of the fixation member through the second channel causes the central axis of the fixation member to have a second orientation relative to the central axis of the body that is different from the first orientation.

14. The glenosphere of claim 13, wherein the first orientation is parallel and the second orientation is not parallel.

15. The glenosphere of claim 1, wherein the flange includes a three apertures, each of the three apertures being configured to receive a respective fixation member therethrough to aid in attaching the glenosphere to bone.

16. A shoulder implant system, comprising:
an attachment structure attachable to a bone of a patient, the attachment structure including:
a base plate having a bone facing surface and an opposing surface; and
a first engagement feature; and
a glenosphere including:
a body having a bone facing surface and an opposing generally spherical articulating surface;
a flange integral with and extending from the body; and
a second engagement feature configured to mate with the first engagement feature such that the glenosphere is coupled to the attachment structure.

17. The shoulder implant system of claim 16, wherein the first engagement feature protrudes from the opposing surface of the base plate and the second engagement feature includes a cavity.

18. The shoulder implant system of claim 16, wherein the flange aids in preventing rocking of the glenosphere relative to the attachment structure.

19. The shoulder implant system of claim 16, wherein the flange extends about less than half of a perimeter of the body.

20. The shoulder implant system of claim 16, wherein the flange includes an aperture that is configured to receive a fixation member therethrough to aid in attaching the glenosphere to bone, a first portion of the aperture defining a first channel for the fixation member and a second portion of the aperture defining a second channel for the fixation member.

* * * * *